US012616606B2

(12) United States Patent
Zerhusen et al.

(10) Patent No.: US 12,616,606 B2
(45) Date of Patent: May 5, 2026

(54) HEAT EXCHANGE SYSTEM FOR PATIENT SUPPORT SURFACE

(71) Applicant: Hill-Rom Services, Inc., Batesville, IN (US)

(72) Inventors: Robert Mark Zerhusen, Cincinnati, OH (US); Nicholas Mann, Cincinnati, OH (US); Neal Wiggermann, Batesville, IN (US); Frank Sauser, Cincinnati, OH (US); Kirsten Emmons, Batesville, IN (US); David Ribble, Indianapolis, IN (US); Darrell L. Borgman, Batesville, IN (US); Charles A. Lachenbruch, Batesville, IN (US); Yongji Fu, Gelugor (MY)

(73) Assignee: Hill-Rom Services, Inc., Batesville, IN (US)

( * ) Notice: Subject to any disclaimer, the term of this patent is extended or adjusted under 35 U.S.C. 154(b) by 519 days.

(21) Appl. No.: 17/878,139

(22) Filed: Aug. 1, 2022

(65) Prior Publication Data

US 2023/0034818 A1 Feb. 2, 2023

Related U.S. Application Data

(60) Provisional application No. 63/228,353, filed on Aug. 2, 2021.

(51) Int. Cl.
| | |
|---|---|
| *A61F 7/00* | (2006.01) |
| *A47C 21/04* | (2006.01) |

(52) U.S. Cl.
CPC ............ *A61F 7/007* (2013.01); *A47C 21/044* (2013.01); *A47C 21/048* (2013.01);
(Continued)

(58) Field of Classification Search
CPC ............ A61F 7/0097; A61F 2007/0057; A61F 2007/0071; A61F 2007/0093;
(Continued)

(56) References Cited

U.S. PATENT DOCUMENTS

| | | | |
|---|---|---|---|
| 8,683,750 B2 | 4/2014 | Gallant et al. | |
| 8,893,329 B2 * | 11/2014 | Petrovski ............. | A47C 31/007 5/724 |

(Continued)

*Primary Examiner* — Justin C Mikowski
*Assistant Examiner* — Deborah Talitha Gedeon
(74) *Attorney, Agent, or Firm* — Price Heneveld LLP

(57) ABSTRACT

A heat exchange system includes a thermoelectric device operably coupled with a support apparatus. The thermoelectric device is configured to reduce a temperature at a first location and increase a temperature at a second location different than the first location. A fan is disposed adjacent to the thermoelectric device. The fan is configured to direct heat generated by the thermoelectric device toward the second location. A controller is communicatively coupled with the thermoelectric device and the fan. The controller is configured to activate the thermoelectric device and the fan to reduce the temperature at the first location and concurrently increase the temperature at the second location. The first location is configured to align with a first area on a patient and the second location is configured to align with a second area on the patient.

15 Claims, 24 Drawing Sheets

(52) U.S. Cl.
CPC .... *A61F 7/0097* (2013.01); *A61F 2007/0057* (2013.01); *A61F 2007/0071* (2013.01); *A61F 2007/0075* (2013.01); *A61F 2007/0093* (2013.01)

(58) Field of Classification Search
CPC ............. A61F 2007/0075; A61F 7/007; A47C 21/044; A47C 21/048
USPC ..... 5/423, 421, 652.1, 652.2, 713, 724, 726, 5/941
See application file for complete search history.

(56) References Cited

U.S. PATENT DOCUMENTS

| | | | | |
|---|---|---|---|---|
| 9,638,442 | B2 | 5/2017 | Makansi et al. | |
| 10,548,788 | B2 | 2/2020 | Lachenbruch et al. | |
| 10,571,162 | B2 | 2/2020 | Makansi et al. | |
| 10,675,434 | B2 | 6/2020 | Van Driel et al. | |
| 10,792,461 | B2 | 10/2020 | Franceschetti et al. | |
| 10,820,714 | B2 | 11/2020 | Boersma et al. | |
| 10,986,934 | B1 | 4/2021 | Youngblood et al. | |
| 2009/0000031 | A1* | 1/2009 | Feher ........................ | A47C 7/74 |
| | | | | 5/423 |
| 2009/0064411 | A1* | 3/2009 | Marquette ................ | A47C 7/74 |
| | | | | 62/3.5 |
| 2011/0092890 | A1 | 4/2011 | Stryker et al. | |
| 2015/0289667 | A1* | 10/2015 | Oakhill .................. | A47C 27/18 |
| | | | | 5/423 |
| 2016/0128487 | A1* | 5/2016 | Eskridge, III ......... | A47C 27/14 |
| | | | | 5/423 |
| 2017/0135884 | A1* | 5/2017 | Lachenbruch ........ | A61F 7/0097 |
| 2017/0181225 | A1* | 6/2017 | Inaba ..................... | B60N 2/565 |
| 2017/0273470 | A1* | 9/2017 | Brykalski ............ | A47C 21/048 |
| 2017/0280883 | A1 | 10/2017 | Diller | |
| 2019/0059603 | A1* | 2/2019 | Griffith ................ | A47C 21/048 |

* cited by examiner 16.5 x 12

12.5 x 10

HEAT EXCHANGE SYSTEM FOR PATIENT SUPPORT SURFACE

CROSS-REFERENCE TO RELATED APPLICATION

This application claims priority to and the benefit under 35 U.S.C. § 119(e) of U.S. Provisional Application No. 63/228,353, filed on Aug. 2, 2021, entitled "HEAT EXCHANGE SYSTEM FOR PATIENT SUPPORT SURFACE," the disclosure of which is hereby incorporated herein by reference in its entirety.

FIELD OF THE DISCLOSURE

The present disclosure generally relates to a heat exchange system, and more particularly to a heat exchange system for a patient support surface.

SUMMARY OF THE DISCLOSURE

According to one aspect of the present disclosure, a heat exchange system includes at least one thermoelectric device operably coupled with a support apparatus. The at least one thermoelectric device is configured to reduce a temperature at a first location and increase a temperature at a second location different than the first location. A heat directing feature is disposed proximate to the at least one thermoelectric device. The heat directing feature is configured to direct heat generated by the at least one thermoelectric device toward the second location. A controller is communicatively coupled with the at least one thermoelectric device. The controller is configured to activate the at least one thermoelectric device to reduce the temperature at the first location and concurrently increase the temperature at the second location. The first location is configured to align with a first area on a patient and the second location is configured to align with a second area on the patient.

According to another aspect of the present disclosure, a support surface assembly includes an outer ticking. A core is disposed within the outer ticking, and the core defines an insertion cavity. A heat exchange system is coupled to the core. The heat exchange system includes a thermally conductive spacer selectively insertable in the insertion cavity. A thermoelectric device is disposed adjacent to the thermally conductive spacer. The thermoelectric device reduces a temperature at a first location via the thermally conductive spacer. A fan is configured to direct heat generated by the thermoelectric device away from the thermoelectric device. A connector extends from the fan to a second location. The connector is thermally conductive and configured to transfer the heat to the second location and, consequently, increase a temperature at the second location.

According to yet another aspect of the present disclosure, a support apparatus includes a frame. A support surface assembly is disposed on the frame and configured to support a patient. A rail is coupled to the frame. A heat exchange system is selectively coupled to the rail. The heat exchange system includes a skin dressing configured to be coupled to the patient. A thermally conductive connector is coupled to the skin dressing. A thermoelectric device is coupled to the thermally conductive connector and configured to reduce a temperature of the skin dressing. The thermoelectric device generates heat. A tubing is coupled to the thermoelectric device and configured to guide heated air warmed by the heat generated by the thermoelectric device to a second location.

According to another aspect of the present disclosure, a support apparatus includes a frame having a deck for supporting a patient thereon. A heat exchange system is coupled to the frame. The heat exchange system includes a compressor. Heating loops are coupled to the compressor, where the heating loops extend along a first location on the deck. Cooling loops are coupled to the compressor where the cooling loops extend along a second location on the deck. The compressor drives a fluid through the heating loops and the cooling loops.

According to still another aspect of the present disclosure, a support surface assembly includes a core defining a first insertion cavity and a second insertion cavity. An outer ticking extends over the core. A first thermoelectric module is selectively disposed within the first insertion cavity. A second thermoelectric module is selectively disposed within the second insertion cavity. Each of the first thermoelectric module and the second thermoelectric module include a support structure defining an airflow channel. A thermoelectric device is coupled with the support structure. A fan is coupled to the support structure and configured to direct air through the airflow channel. A controller is in communication with the first thermoelectric module and the second thermoelectric module. The controller is configured to selectively and independently direct a current through the first thermoelectric module and the second thermoelectric module to adjust a temperature of a corresponding area of the outer ticking.

According to one aspect of the present disclosure, a patient temperature regulating system includes a first thermoelectric module having a first thermoelectric device. A second thermoelectric module has a second thermoelectric device. At least one user device is configured to receive an input. A controller is in communication with each of the first thermoelectric module, the second thermoelectric module, and the at least one user device. The controller is configured to receive a first input relating to the first thermoelectric module from the at least one user device, direct a current in a first direction through the first thermoelectric device to produce a first temperature effect, receive a second input relating to the second thermoelectric module from the at least one user device, and direct a current in a second direction through the second thermoelectric device to produce a second temperature effect.

These and other features, advantages, and objects of the present disclosure will be further understood and appreciated by those skilled in the art by reference to the following specification, claims, and appended drawings.

DETAILED DESCRIPTION

Figure 1:
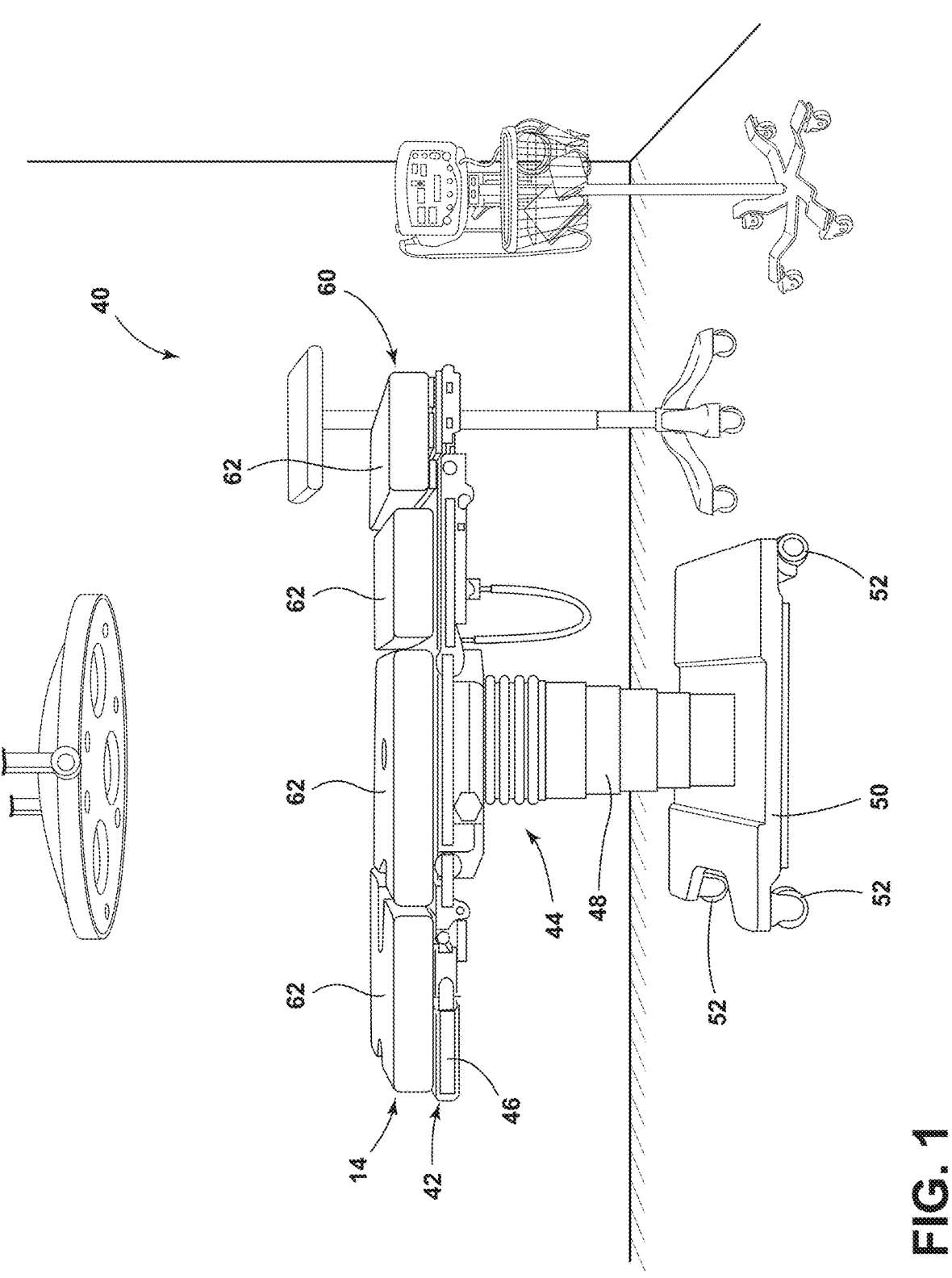
FIG. 1 is a side perspective view of an operating table within a surgical suite, according to the present disclosure.

The present illustrated embodiments reside primarily in combinations of method steps and apparatus components related to a heat exchange system for a patient support surface. Accordingly, the apparatus components and method steps have been represented, where appropriate, by conventional symbols in the drawings, showing only those specific details that are pertinent to understanding the embodiments of the present disclosure so as not to obscure the disclosure with details that will be readily apparent to those of ordinary skill in the art having the benefit of the description herein. Further, like numerals in the description and drawings represent like elements.

For purposes of description herein, the terms "upper," "lower," "right," "left," "rear," "front," "vertical," "horizontal," and derivatives thereof, shall relate to the disclosure as oriented in FIG. 1. Unless stated otherwise, the term "front" shall refer to a surface closest to an intended viewer, and the term "rear" shall refer to a surface furthest from the intended viewer. However, it is to be understood that the disclosure may assume various alternative orientations, except where expressly specified to the contrary. It is also to be understood that the specific structures and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

The terms "including," "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element preceded by "comprises a . . . " does not, without more constraints, preclude the existence of additional identical elements in the process, method, article, or apparatus that comprises the element.

With reference to FIGS. 1-26, reference numeral 10 generally designates a heat exchange system that includes at least one thermoelectric device 12 operably coupled with a support apparatus 14. The thermoelectric device 12 is configured to reduce the temperature at a first location 16 and increase a temperature at a second location 18, which is different from the first location 16. A fan 20 is configured to direct heat generated by the thermoelectric device 12 to the second location 18. The controller 22 is communicatively coupled with the thermoelectric device 12 and the fan 20. The controller 22 is configured to activate the thermoelectric device 12 and the fan 20 to reduce the temperature at the first location 16 and concurrently increase the temperature at the second location 18. The first location 16 is configured to align with a first area 24 on a patient and the second location 18 is configured to align with a second area 26 on the patient.

When at a medical facility, the patient may be transported between several areas or units. For example, the patient may be transferred between different departments or units on different floors within the medical facility depending on a treatment or procedure to be received. The patient may arrive at the medical facility for one or more surgical procedures and be included in a perioperative environment, which includes a preoperative phase, an intraoperative phase, and postoperative phase based on the timing relative to a surgical procedure.

During the stay at the medical facility, the patient is generally supported or positioned on the support apparatus 14, which may have a variety of configurations depending on the unit or department. A caregiver may provide treatment or therapy to the patient using the support apparatus 14 and may also utilize features of the support apparatus 14 to increase the comfort of the patient. For example, the caregiver may provide treatment for reducing the development of a pressure injury, which includes localized damage to the skin and underlying soft tissue. Generally, the pressure injury is developed over a bony prominence and may be related to use of a medical device or as a result of intense pressure, prolonged pressure, pressure in combination with sheer, or combination thereof. Exemplary locations or areas prone to developing pressure injuries include the sacral region, ischial tuberosity, heels, etc. In certain aspects, intraoperative pressure injuries may be treated by the caregiver. Intraoperative pressure injuries may include deep tissue injuries that are discovered post-surgery within a subsequent care environment (e.g., a medical/surgical unit, and intensive care unit, other postoperative care, step down unit, home, etc.).

The risk of the patient developing a pressure injury is cumulative during the time the patient is at the medical facility. A variety of factors contribute to the tolerance of the soft tissue for pressure and shear (e.g., mechanical load), including microclimate, nutrition, perfusion, comorbidities, and the condition of the soft tissue. For example, moisture often causes the skin to soften, which can increase the likelihood of the pressure injury developing. Additionally, temperature can increase metabolic processes, which can speed up breakdown of skin. Also, fluid retention may lead to more pressure, which can lead to an increase in temperature. One or more risk assessment tools, such as the Braden scale, the Norton scale, the Waterlow scale, the Scott Triggers, or a combination thereof, are generally utilized to determine a risk score or risk assessment for developing pressure injuries.

The caregiver may provide treatment to reduce these factors and, consequently, reduce the likelihood of developing the pressure injury or reduce the severity of the pressure injury using the heat exchange system 10 disclosed herein. The heat exchange system 10 may be utilized with different configurations of the support apparatus 14, as well as within different units or departments of the medical facility. The heat exchange system 10 may have a variety of configurations depending on the support apparatus 14, the unit, the patient, the treatment to be provided, etc.

Figure 2:
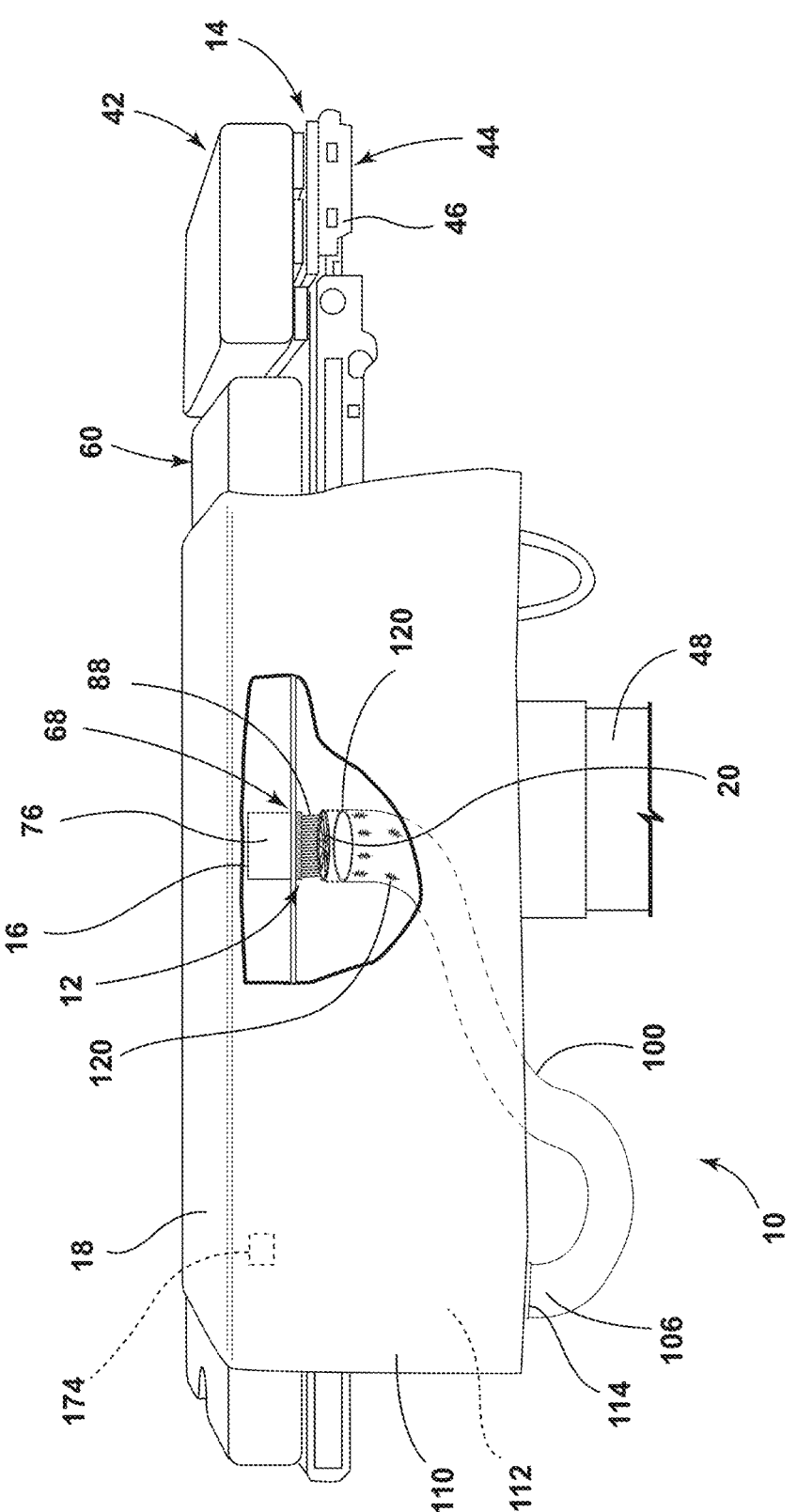
FIG. 2 is a partial side perspective view of an operating table with a heat exchange system and an accessory with a portion of the operating table and the accessory removed, according to the present disclosure.

Referring to FIGS. 1 and 2, the heat exchange system 10 may be utilized within a surgical suite 40 of the medical facility. In the surgical suite 40, the support apparatus 14 is configured as a surgical or operating table 42. In the illustrated example, the operating table 42 includes a frame 44 having a deck 46 for supporting the patient thereon, a pedestal 48, and a base support 50. The pedestal 48 extends between the deck 46 and the base support 50. The pedestal 48 is generally centrally located relative to the deck 46; however, it is contemplated that more than one pedestal 48 may extend between the deck 46 and the base support 50. The base support 50 generally includes rollers 52, allowing the operating table 42 to be transportable around the surgical suite 40 or otherwise transportable about the medical facility.

The deck 46 is generally movable relative to the pedestal 48. The deck 46 may tilt, rotate, or otherwise move relative to the pedestal 48. Additionally, the deck 46 may include multiple segments that may be independently movable relative to one another allowing movement of a certain portion of the deck 46 separately. The deck 46 generally has a modular construction that allows access to items positioned on the deck 46 from an area under the deck 46. This configuration of the deck 46 is advantageous for providing connections to items on the deck 46, such as the heat exchange system 10, while stowing the connections (e.g., cords, wiring, tubing, etc.) in a location that does not substantially interfere with the caregiver or the surgical procedure.

A support surface assembly 60 is positioned on the deck 46 and configured to support the patient thereon. The support surface assembly 60 may be configured as a mattress, a mattress pad or pads, a coverlet, or other support features. The example illustrated in FIG. 1, the support surface assembly 60 includes multiple support sections 62 arranged across the deck 46; however, the support surface assembly 60 may include a single support section 62 extending across the deck 46. Each of the multiple support sections 62 and the single support section 62 configurations generally have substantially similar constructions. Alternatively, different supports sections 62 may be utilized with different aspects of the heat exchange system 10 to provide a warming effect, a cooling effect, or a combination thereof.

During the surgical procedure in the surgical suite 40, the caregiver or caregiving team works to maintain a core temperature of the patient to prevent hypothermia, which is generally defined as a core temperature of less than 35° C. During the surgical procedure, there is a risk of hypothermia because the metabolic rate of the patient is reduced, the surgical suite 40 is generally at a cooler temperature, and the vasoconstriction response of the patient is blunted. The caregiver works to maintain normothermia throughout the surgical procedure, as well as during preoperative and postoperative periods. Normothermia is generally defined as a core temperature of at least 36° C. Milder reductions in core temperature may affect the recovery, length of stay, infection rate, and cardiovascular problems. However, it is also advantageous to cool or reduce a temperature of selected areas on the patient that may be at higher risk of developing pressure injuries.

Warming the patient may increase the risk of pressure injury as warm skin breaks down faster. Therefore, warming the patient to achieve normothermia generally conflicts with cooling the patient for preventing pressure injuries. Use of the heat exchange system 10 may assist the caregiver in maintaining normothermia, as well as reducing the temperature in select areas 24 to reduce the risk of developing the pressure injury for the surgical patient. The heat exchange system 10 may be utilized to concurrently or simultaneously cool areas 24 of the patient where pressure injuries are likely to occur as well as warm other areas 26 of the patient to maintain normothermia or for patient comfort.

Figure 3:
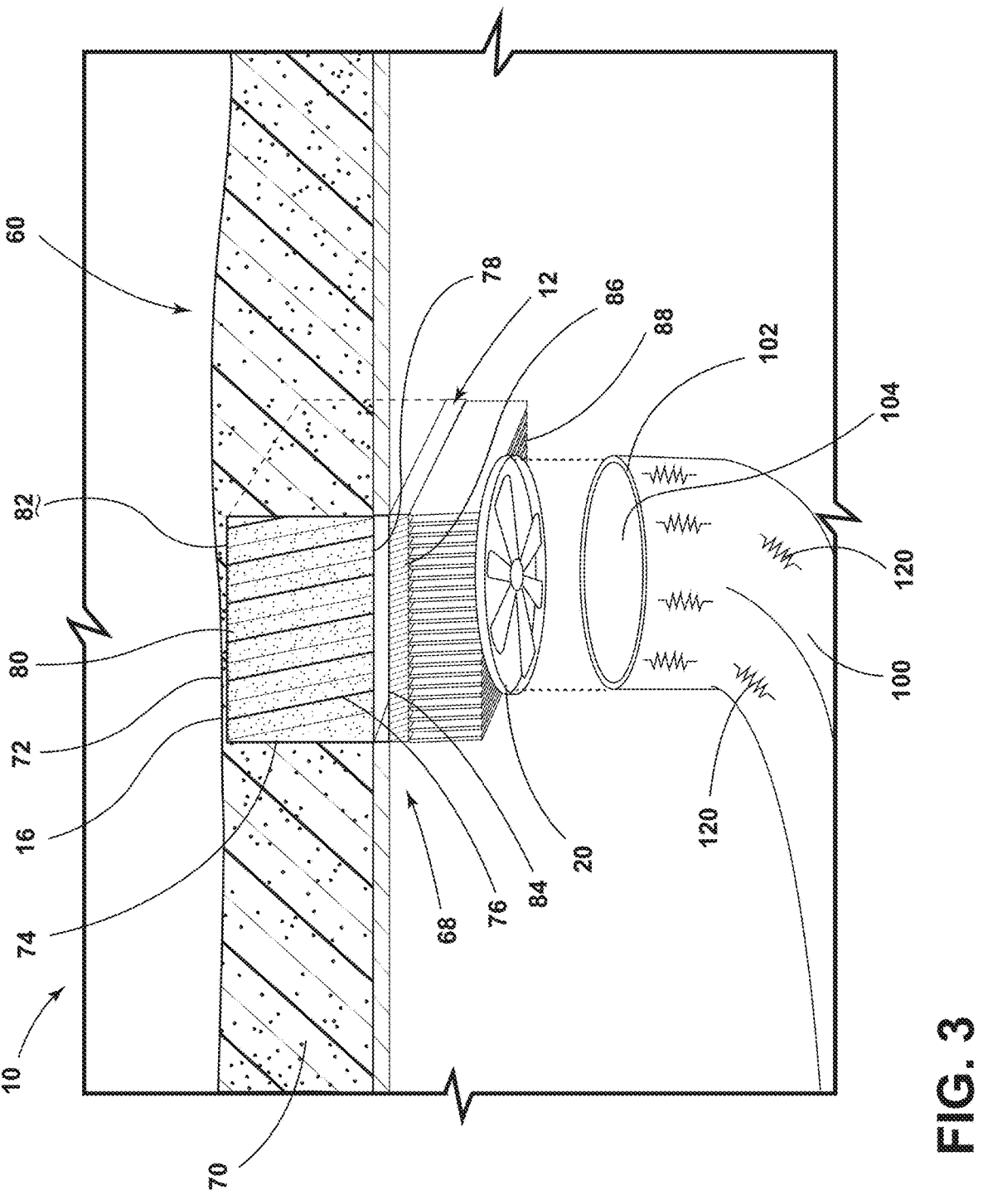
FIG. 3 is a partial bottom perspective view of a heat exchange system with a thermally conductive spacer within a core of a support surface and a thermoelectric device, according to the present disclosure.

Referring to FIGS. 1-3, the heat exchange system 10 is coupled to the operating table 42. The heat exchange system 10 includes a temperature regulating device 68 for generating at least one of a cooling temperature effect and a warming temperature effect. In the example illustrated in FIG. 2, the temperature regulating device 68 is configured as the thermoelectric device 12. The thermoelectric device 12 may be a thermoelectric cooling (TEC) device or similar device, which operates to cool an area on one side of the thermoelectric device 12 and consequently generates heat on an opposing side of the thermoelectric device 12.

The support surface assembly 60 includes a core 70 surrounded by an outer ticking 72. The core 70 is generally a foam material that provides support for the patient thereon. The foam material may be a non-thermally conductive material. The core 70 may define at least one insertion cavity 74, which may be accessible from the area under the deck 46 or may be accessible when the outer ticking 72 is removed. The cavity 74 or cavities 74 may be defined in a single component of the core 70. Alternatively, the core 70 may be constructed of multiple foam modules and removing select modules may form the cavity 74 or cavities 74.

Referring still to FIG. 2, as well as FIG. 3, a thermally conductive spacer 76 is selectively positionable and insertable in the cavity 74. The thermally conductive spacer 76 may be constructed of any thermally conductive material, such as a thermally conductive foam. The thermoelectric device 12 is coupled to a bottom 78 of the thermally conductive spacer 76, while a top 80 of the thermally conductive spacer 76 is positioned proximate to a top surface 82 of the outer ticking 72. In this way, the thermoelectric device 12 is spaced from the top surface 82 where the patient is supported.

As previously stated, the thermoelectric device 12 operates to cool an area on one side of the thermoelectric device 12 while generating heat on the opposing side. A first side 84 of the thermoelectric device 12 is coupled to the bottom 78 of the thermally conductive spacer 76. The first side 84 is a cool side of the thermoelectric device 12, which operates to draw heat from the thermally conductive spacer 76 and, consequently, from the patient on the thermally conductive spacer 76 to cool the corresponding area on the outer ticking 72 and the area 24 on the patient.

A second side 86 of the thermoelectric device 12 generates heat as a result of cooling the first side 84. A heatsink or cooling fins 88 are operably coupled to the second side 86 of thermoelectric device 12. The cooling fins 88 increase a surface area that allows the heat to be directed away from the thermoelectric device 12 and subsequently utilized by the heat exchange system 10.

A heat directing feature is included in the heat exchange system 10 to direct the heat away from the first location 16 and toward or to the second location 18. In various aspects, the heat directing feature may be configured as the fan 20, a blower, a heatsink, a conductive cooling material, a liquid pump, or another device to direct heat or warmed air in a predefined direction or path.

In examples where the heat directing feature is the fan 20, the fan 20 is disposed proximate to the cooling fins 88. The fan 20 is configured to direct the heat away from the thermoelectric device 12 and, consequently, away from the thermally conductive spacer 76. The fan 20 may be positioned in any practicable location to direct the warmed air away from the first location 16.

Referring still to FIGS. 2 and 3, the heat exchange system 10 may include a tube or tubing 100 operably coupled with the thermoelectric device 12. In examples having the tubing 100, a receiving end 102 of the tubing 100 is disposed adjacent to the fan 20. The tubing 100 operates to receive warm air directed by the fan 20, which is warmed by the heat generated from the thermoelectric device 12. The tubing 100 provides an airflow passage 104 for directing or guiding the heated air away from the first location 16 on the support apparatus 14 (e.g., where the thermally conductive spacer 76 is located) to the second location 18, which is spaced from the first location 16. The heat byproduct from the thermoelectric device 12 is captured and utilized by the heat exchange system 10.

The heated air is released toward the second location 18 from a venting end 106 of the tubing 100. In various examples, a secondary device or accessory may be coupled with the heat exchange system 10 to assist in warming the second location 18. In the illustrated example of FIGS. 2 and 3, the accessory utilized with the heat exchange system 10 is a warming or forced-air blanket 110. The blanket 110 defines an internal cavity 112 that allows airflow to be directed therethrough. The venting end 106 is coupled to an inlet port 114 of the blanket 110, allowing the heated air to be directed from the tubing 100 into the internal cavity 112 of the blanket 110 to warm the area 26 of the patient in contact with or under the blanket 110. It is also contemplated that the venting end 106 may be coupled with a second thermally conductive spacer 76 to warm the area 26.

The caregiving team operates to maintain normothermia in the surgical patient by maintaining a higher core temperature. The caregiving team also operates to reduce the temperature of select areas 24 on the patient that are more susceptible to developing pressure injuries. Accordingly, the thermally conductive spacer 76 is positioned in the support surface assembly 60 at the first location 16, which corresponds with the first area 24 on the patient to be cooled. The first area 24 is generally an area that has a higher likelihood of developing the pressure injury. The thermoelectric device 12 is coupled to the thermally conductive spacer 76 to cool the first location 16. The tubing 100 extends between the thermoelectric device 12 and the blanket 110 or other accessories, which is disposed over the patient during the surgical procedure.

Once activated, the heat exchange system 10 operates to cool the first area 24 at the first location 16 by using the thermoelectric device 12. Additionally, the heat exchange system 10 utilizes the heat generated by the thermoelectric device 12 and directs the warmed air to the internal cavity 112 of the blanket 110, which operates to warm the second area 26 of the patient. Accordingly, the first area 24 may be cooled at the same time the second area 26 is warmed. While a single thermally conductive spacer 76 is illustrated in FIGS. 2 and 3, the heat exchange system 10 may utilize multiple thermally conductive spacers 76 that align with each area 24 of the patient that is at risk of pressure injury development. It is contemplated that each thermally conductive spacer 76 may utilize a corresponding thermoelectric device 12 to provide independent and selective control over the temperature at each at-risk area 24.

Referring still to FIGS. 2 and 3, in certain scenarios, additional heat may be utilized by the heat exchange system 10. This additional heat may be more heat than is produced by the thermoelectric device 12. If additional heat is to be utilized by the heat exchange system 10, resistive elements 120 may be coupled to the tubing 100. The resistive elements 120 generate the additional heat as an electrical current passes through the resistive elements 120 to increase an air temperature within the tubing 100. The air traveling through the tubing 100 is heated further by the heat generated by the resistive elements 120. The additional heat may be utilized to warm select areas 26 of the patient, assist in maintaining normothermia, improve comfort of the patient, or a combination thereof.

Figure 4:
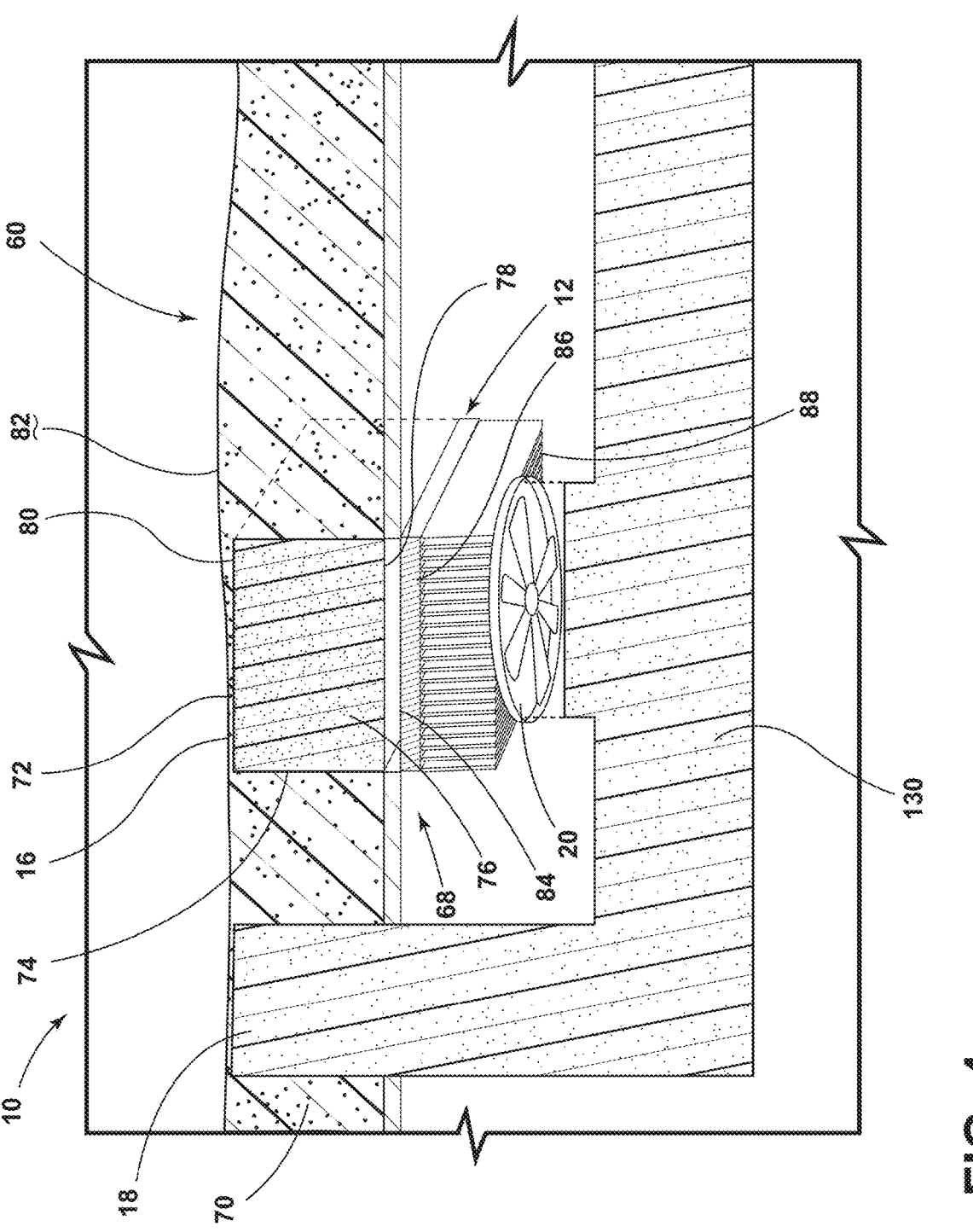
FIG. 4 is a partial bottom perspective view of a heat exchange system with a thermally conductive spacer at a first location with a core of a support surface, a thermoelectric device, and a thermally conductive connector extending to second locations within the core, according to the present disclosure.

Referring to FIG. 4, the heat exchange system 10 may be more fully incorporated into the support surface assembly 60. In the illustrated example, the heat exchange system 10 utilizes a thermally conductive connector 130 that extends at least partially through the core 70 of the support surface assembly 60. The thermally conductive connector 130 may generally be surrounded by the non-thermally conductive core 70, providing a thermal path for directing the heat from the thermoelectric device 12 to the second location 18 or multiple second locations 18. Additionally or alternatively, the thermally conductive connector 130 may extend from the thermoelectric device 12, below the deck 46 of the operating table 42, and then through an additional cavity 74 in the core 70. In such examples, the heat is transferred from the thermoelectric device 12, through the thermally conductive connector 130, and toward the top surface 82 of the outer ticking 72 to warm the patient at the second location 18. It is contemplated that the thermally conductive connector 130 may be flexible to be adjustable to different second locations 18.

Figure 5:
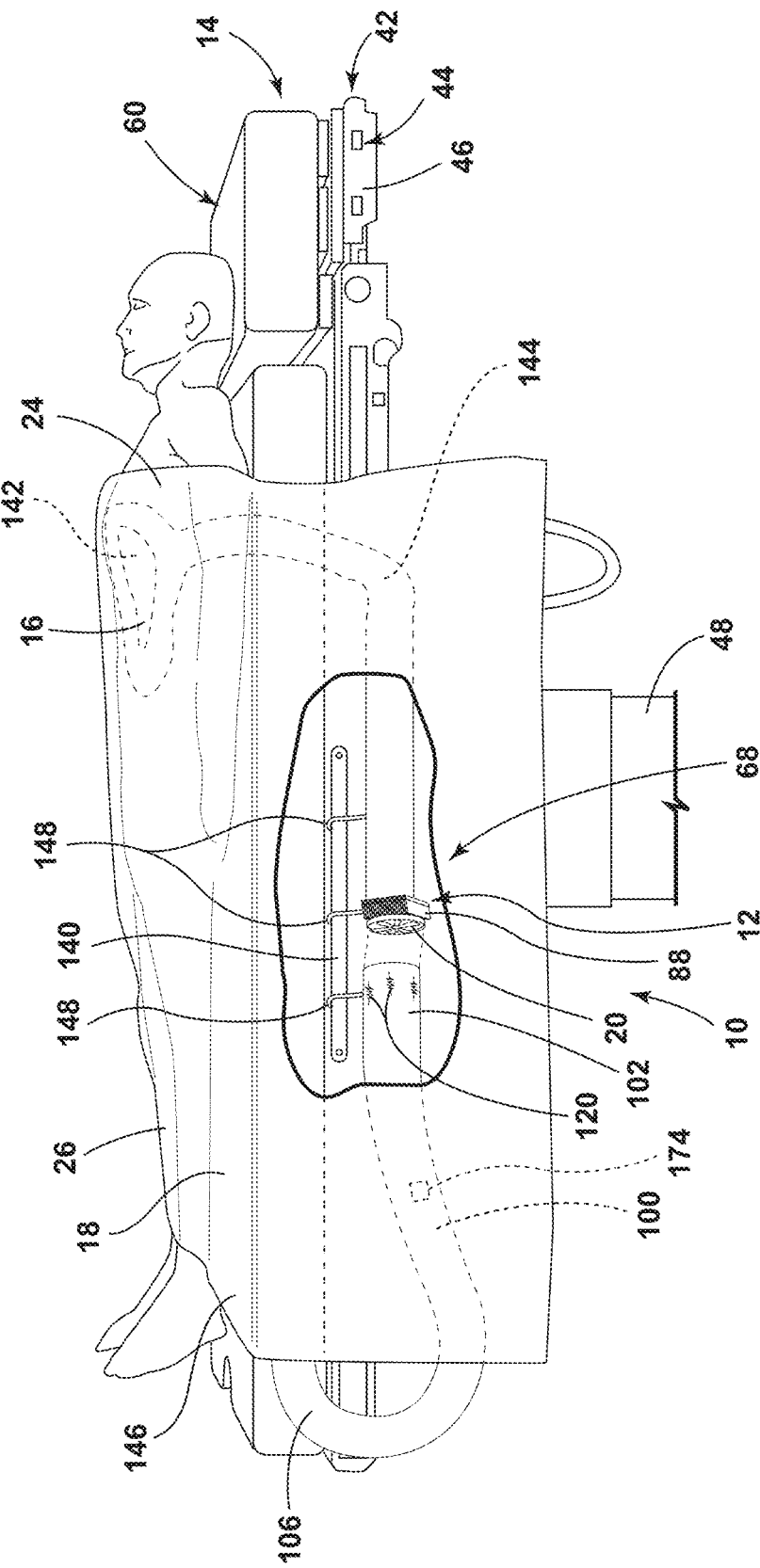
FIG. 5 is a partial side perspective view of an operating table with a heat exchange system coupled to an accessory rail with a portion of the operating table and an accessory removed, according to the present disclosure.
Figure 6:
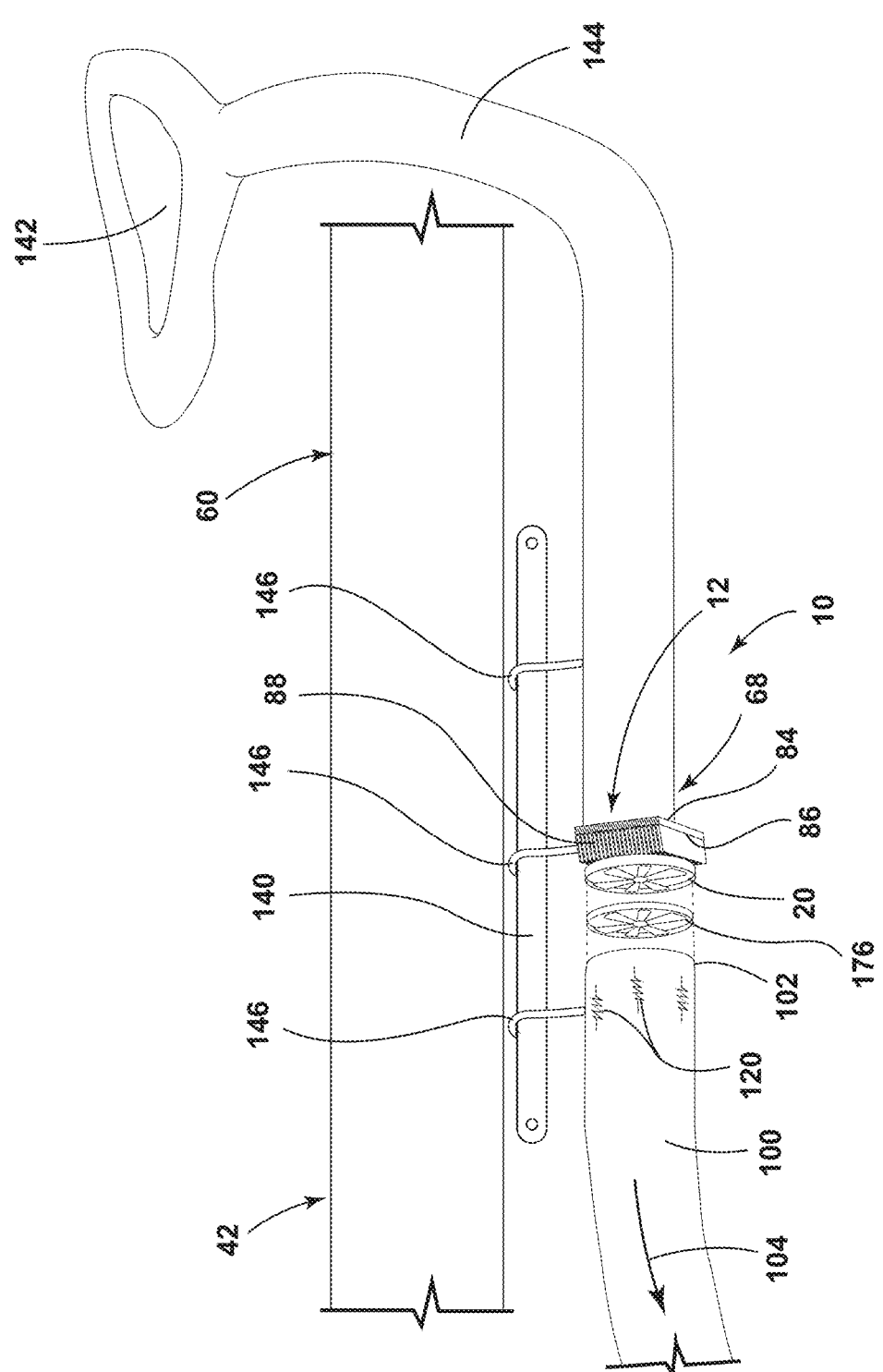
FIG. 6 is a partial side perspective view of a portion of a heat exchange system with a skin dressing thermally coupled with a thermoelectric device, according to the present disclosure.

With reference to FIGS. 5 and 6, an additional or alternative configuration of the heat exchange system 10 is illustrated, which may be selectively coupled to the operating table 42 via an accessory rail 140. In this configuration, the heat exchange system 10 may be a separate assembly that may be added to or removed from the operating table 42, which can provide increased flexibility in the surgical suite. The accessory rail 140 is generally coupled to the deck 46 and operates to secure various accessories utilized for the surgical procedure or the caregiving team.

The heat exchange system 10 includes a skin dressing 142, which is configured to be adhered or otherwise coupled to or disposed on the skin of the patient. The skin dressing 142 is generally a flexible padded patch. The skin dressing 142 may be a designated dressing or patch for the heat exchange system 10 or may be part of a padded dressing used for pressure injury prevention. The skin dressing 142 is coupled with a thermally conductive connector 144. The thermally conductive connector 144 may surround the skin dressing 142, may be an extension of the skin dressing 142, or may be otherwise thermally coupled with the skin dressing 142. The thermally conductive connector 144 extends from the skin dressing 142 to the first side 84 of the thermoelectric device 12. In this way, when the thermoelectric device 12 is activated, the cool first side 84 of the thermoelectric device 12 draws heat away from the patient through the thermally conductive connector 144 and the skin dressing 142.

The heat generated by the second side 86 of the thermoelectric device 12 warms the air adjacent to the fan 20, and the fan 20 may direct the warmed air through the tubing 100. The tubing 100 is coupled to the thermoelectric device 12 and may direct the heated air toward the accessory. The heat exchange system 10 may then warm air at the second location 18, which may be an area above the deck 46 and below the accessory, such as a drape 146. The drape 146 is often placed over the surgical patient during the surgical procedure to assist in maintaining a sterile environment. The tubing 100 may expel the warm air below the drape 146 to warm the patient. Accordingly, the first area 24 where the skin dressing 142 is located is cooled while the second area 26 covered by the drape 146 is simultaneously warmed. While a single skin dressing 142 is illustrated, multiple skin dressings 142 may be thermally coupled with the thermoelectric device 12.

The heat exchange system 10 includes multiple coupling features 148 for coupling the heat exchange system 10 on the operating table 42. The coupling features 148 may be hooks, loops, or other features that selectively couple to the accessory rail 140. For example, one coupling feature 148 may extend from each of the thermally conductive connector 144, the thermoelectric device 12, and the tubing 100 to support the heat exchange system 10. Additional coupling features 148 or additional locations on the heat exchange system 10 may be utilized without departing from the teachings herein. Coupling the heat exchange system 10 to the accessory rail 140 may generally move the heat exchange system 10 away from a work area of the caregiving team and reduce interference with the surgical procedure.

Referring still to FIGS. 5 and 6, the heat exchange system 10 may also include the resistive elements 120. The resistive elements 120 are disposed proximate to the receiving end 102 of the tubing 100 or elsewhere along the tubing 100 to provide the additional heat for warming the air traveling through tubing 100.

Figure 7:
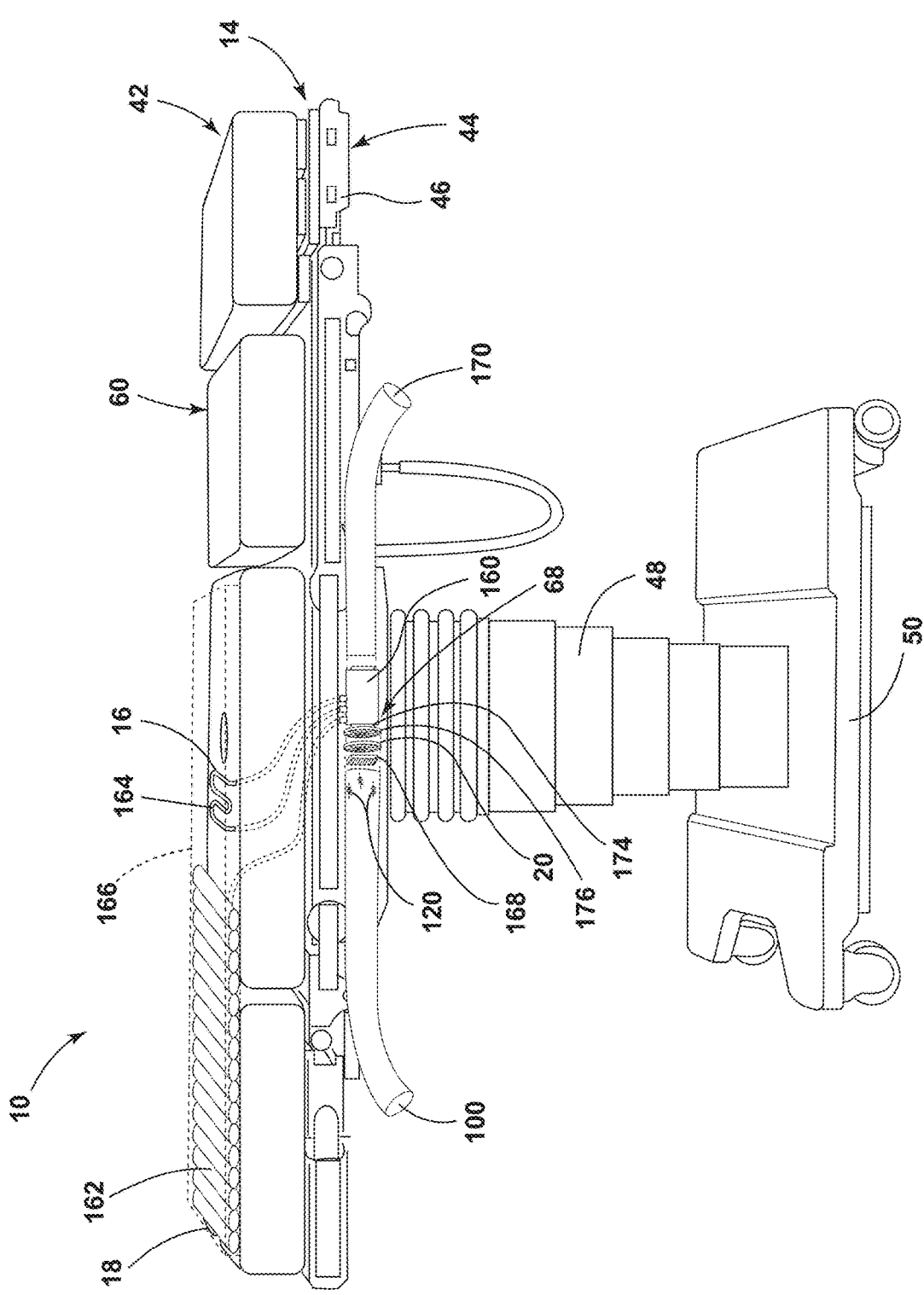
FIG. 7 is a side perspective view of an operating table with a heat exchange system having a compressor, heating loops, and cooling loops, according to the present disclosure.

Referring to FIG. 7, in an additional or alternative configuration of the heat exchange system 10, the temperature regulating device 68 may be configured as a compressor 160 for heating and cooling various zones along the deck 46. Heating loops 162 are operably coupled with the compressor 160 and extend over the second location 18 on the deck 46. Additionally, cooling loops 164 are operably coupled to the compressor 160 and extend over the first location 16 on the deck 46. The heat exchange system 10 may utilize a fluid, such as air or a coolant driven by the compressor 160, to provide the temperature effects generated by the heating loops 162 and the cooling loops 164.

In certain aspects, the compressor 160 may be a separate or external component coupled to the operating table 42, such as via the accessory rail 140. In such examples, the heating loops 162 and the cooling loops 164 may be included in a topper 166 placed over the deck 46 or the support surface assembly 60. In this way, the heat exchange system 10 is a separate assembly that may be added or removed from the operating table 42.

In additional or alternative aspects, the compressor 160 may be integrated into the operating table 42. In such examples, the heating loops 162 and the cooling loops 164 may be integrated into the deck 46. The zones to be cooled and heated may be predefined based on a more standard position of the patient on the operating table 42 or may be alternated by the compressor 160. Further, the heating loops 162 and the cooling loops 164 may be positioned based on common areas to be cooled for pressure injury prevention and warmed for maintaining normothermia.

The heat exchange system 10 may include an additional heater element 168 operably coupled with at least one of the compressor 160, the heating loops 162, and the tubing 100. In such examples, the additional heater element 168 may provide additional heat for warming the heating loops 162 and/or heating the air traveling through the tubing 100.

The heat exchange system 10 illustrated in FIG. 7 includes the tubing 100, which extends from at least one of the compressor 160 and the heater element 168. The air heated by the compressor 160 and/or the heater element 168 may travel along the tubing 100 to provide warm air for the accessory, such as the blanket 110. The tubing 100 may also include the resistive elements 120 in combination with or in lieu of the heater element 168. The use of the accessory may provide more flexibility to the heat exchange system 10 that includes the heating loops 162 and the cooling loops 164.

Additionally, the heat exchange system 10 may include a hose 170 coupled with the compressor 160. The compressor 160 generally provides cool air to the hose 170. The hose 170 may be coupled with another accessory utilized for the patient or the caregiving team. For example, surgeons may utilize devices for providing a cooling temperature effect to the surgeon during the surgical procedure. The hose 170 may be selectively coupled with this device to provide the cooling temperature effect to the surgeon. Accordingly, the heat exchange system 10 may provide the cooling temperature effect to the patient and the caregiving team.

Referring again to FIGS. 1-7, the heat exchange system 10 is utilized to warm the patient during the surgical procedure while cooling selected areas that are at higher risk for developing a pressure injury. The heat exchange system 10 may warm, for example, selected zones or the remainder of the deck 46 of the operating table 42. Warming the operating table 42 allows the patient to be warmed without obstructing the surgical site or interfering with the work area of the caregiving team. The heat exchange system 10 operates to simultaneously cool and heat two different locations. The two locations may be on the patient, on the operating table 42, or a combination thereof.

Use of the heat exchange system 10 on the operating table 42 may be advantageous as the position of the patient on the operating table 42 is static. The patient is placed in a specific position that allows the greatest access to the patient for the surgical procedure. This specific position may be a standard or common position for many surgical procedures. Once the patient is placed on the operating table 42, the patient generally remains in the same position for the duration of the surgical procedure. Accordingly, the location of bony prominences is substantially consistent for the patient on the operating table 42 and remains consistent as the patient generally does not move during the surgical procedure. Having the heat exchange system 10 integrated into the operating table 42 may allow predefined zones on the operating table 42 for heating and cooling based on the position the patient is typically in on the operating table 42.

Additionally or alternatively, the tubing 100 and/or the thermally conductive connector 130 may also direct the heated air through zones in the support surface assembly 60 or an additional support surface positioned on the support surface assembly 60, such as an air-permeable topper or a Microclimate Management (MCM) System topper. Accordingly, the heat exchange system 10 may warm the deck 46 of the operating table 42, an interior of an accessory such as the blanket 110, an area between the deck 46 and the accessory such as the drape 146, a topper, or a combination thereof.

Referring still to FIGS. 1-7, in examples where the heat exchange system 10 includes the resistive elements 120, the heat exchange system 10 may also include or be in communication with a thermometer or temperature sensor 174. The temperature sensor 174 may be disposed within the support surface assembly 60, as illustrated in FIG. 2, within the airflow passage 104 of the tubing 100, as illustrated in FIG. 5, or another practicable location. The temperature sensor 174 is positioned to sense the temperature of the heated or warmed air being delivered to the patient.

The controller 22 is generally in communication with the temperature sensor 174. When the sensed temperature is below a predefined temperature, the controller 22 and/or the heat exchange system 10 may increase the temperature being delivered to the patient by running the current through the resistive elements 120. Accordingly, the temperature of the air being used to warm the patient may be monitored and adjusted to provide air warmed to a selected or predefined temperature. This may be advantageous for increasing the comfort of the patient and/or maintaining normothermia.

In various examples, the heat exchange system 10 may include a temperature control fan 176 in addition or alternatively to the fan 20. The temperature control fan 176 may assist in controlling the temperature of the air directed from the temperature regulating device 68 (e.g., the thermoelectric device 12, the compressor 160, etc.). According to various aspects, activation of the temperature control fan 176 may control a direction the warmed air is guided. For example, when the temperature control fan 176 is activated, more air is guided along a first path, and when the temperature control fan 176 is off or deactivated, more air is guided along a second path.

In a non-limiting example, when the temperature control fan 176 is activated, the air is guided along the first path toward the patient, and when the temperature control fan 176 is deactivated, the air is guided along the second path toward an exhaust (e.g., not used for warming the patient). In another non-limiting example, when the temperature control fan 176 is activated, the air is guided along the first path toward the exhaust, and when the temperature control fan 176 is deactivated, the air is guided along the second path toward the patient. In this way, when additional heated air is to be directed to the patient, the heat exchange system 10 may function to provide the warmed air to the patient, and when the patient is sufficiently warmed, as determined by at least one of the controller 22 and the heat exchange system 10, the heat exchange system 10 may divert the heated air to the exhaust. This configuration provides for active control and management for warming the patient. The temperature sensor 174 may be utilized to determine when to divert the warmed air to the exhaust.

Figure 8:
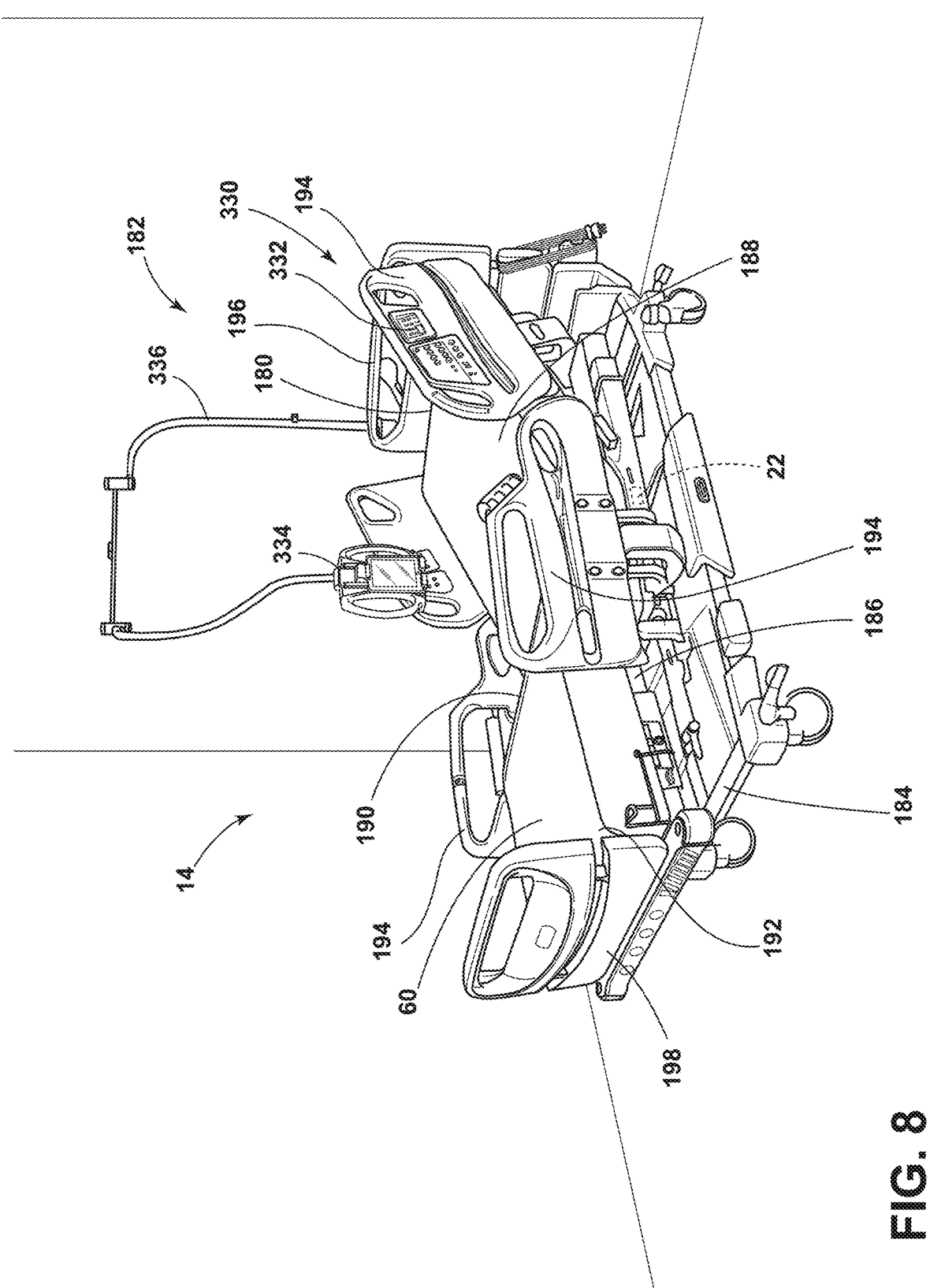
FIG. 8 is a side perspective view of a medical bed in a patient room, according to the present disclosure.

Referring to FIG. 8, an additional or alternative configuration of the heat exchange system 10 is illustrated where the support apparatus 14 is configured as a bed 180 in a patient room 182. The bed 180 includes a base frame 184 coupled to an upper frame 186. The upper frame 186 is adjustable relative to the base frame 184 (e.g., raise, lower, tilt, etc.). Additionally, the upper frame 186 generally includes multiple segments 188, 190, 192 that are independently adjustable relative to one another, allowing the upper frame 186 to articulate between various positions (e.g., an elevated head region, elevated foot region, etc.). The bed 180 generally includes actuation assemblies for adjusting the upper frame 186 and the segments 188, 190, 192. The bed 180 also includes side rails 194, which are generally adjustable between a raised position and a lowered position. Further, the bed 180 includes a headboard 196 and a footboard 198, which may be fixedly coupled to the upper frame 186 or removable to provide increased access to the patient.

Figure 9:
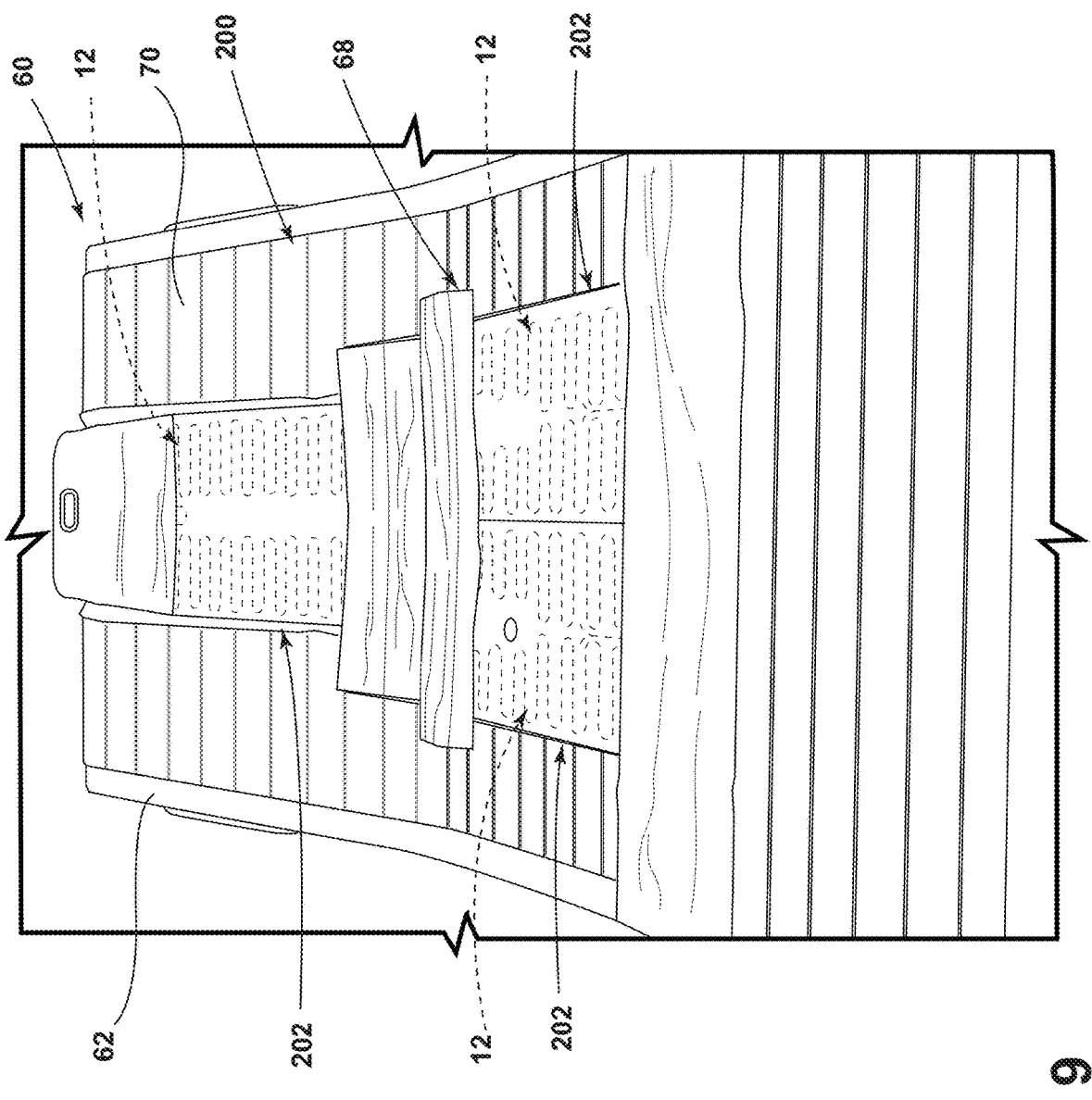
FIG. 9 is a partial top perspective view of an interior of a support surface assembly having core blocks and thermoelectric modules, according to the present disclosure.

Referring still to FIG. 8, as well as to FIG. 9, the support surface assembly 60 is generally positioned on the upper frame 186. The support surface assembly 60 may be configured as the multiple support sections 62 or the single support section 62. The support sections 62 may be disposed within the same outer ticking 72 or separate outer tickings 72 without departing from the teaching herein.

In the example illustrated in FIG. 9, the support surface assembly 60 includes multiple core blocks 200 that are disposed within the same outer ticking 72 to form a single mattress. The core blocks 200 are each generally constructed of a foam material, which may be a non-thermally conductive material. The core blocks 200 may be arranged in a predefined configuration, or alternatively may be selectively interchangeable between different positions based on the configuration of the heat exchange system 10.

The heat exchange system 10 includes one or multiple temperature regulating devices 68, which are configured as thermoelectric modules 202. Each thermoelectric module 202 is disposed within one of the cavities 74 defined by the core 70. The cavities 74 may be in different positions based on the arrangement of the core blocks 200. In this way, the core blocks 200 may be moved to provide for different locations or numbers of cavities 74. Additionally or alternatively, the core blocks 200 and the thermoelectric modules 202 may be in predefined configurations within the support surface assembly 60. In such examples, the support surface assemblies 60 with different configurations of the heat exchange system 10 may be interchanged to provide the configuration with the selected arrangement for the patient.

Each thermoelectric module 202 has a substantially similar construction, though the thermoelectric modules 202 may be different sizes based on the location relative to the patient as discussed herein. Each thermoelectric module 202 may include a support structure 204, the thermoelectric device 12, and the fan 20. The thermoelectric device 12 may be incorporated into the support structure 204 making the thermoelectric modules 202 a self-contained unit. In the example illustrated in FIG. 9, three thermoelectric modules 202 are illustrated, however fewer or additional thermoelectric modules 202 may be included in the heat exchange system 10 without departing from the teachings herein.

Figure 10:
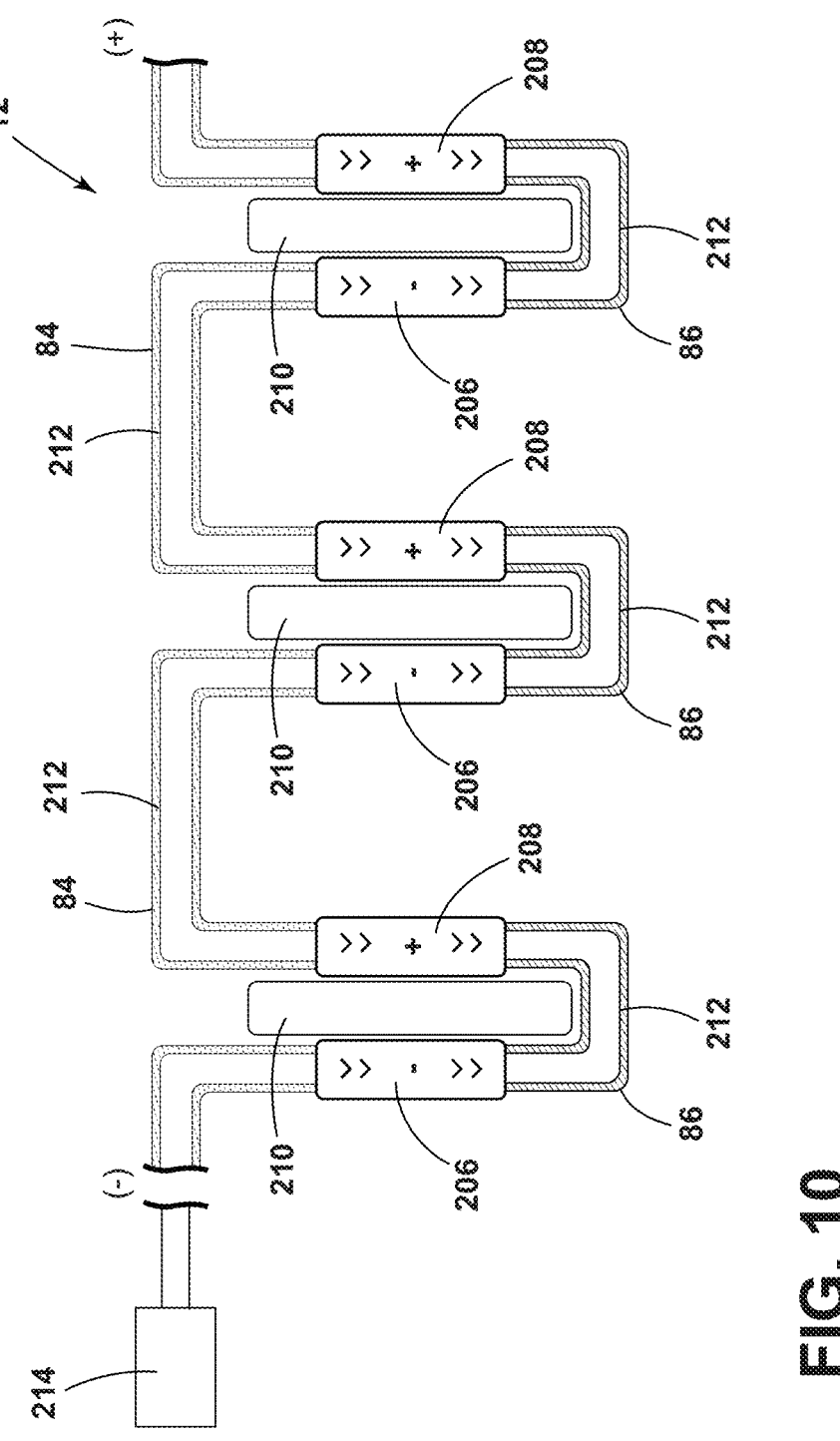
FIG. 10 is a schematic diagram of a thermoelectric device, according to the present disclosure.
Figure 11:
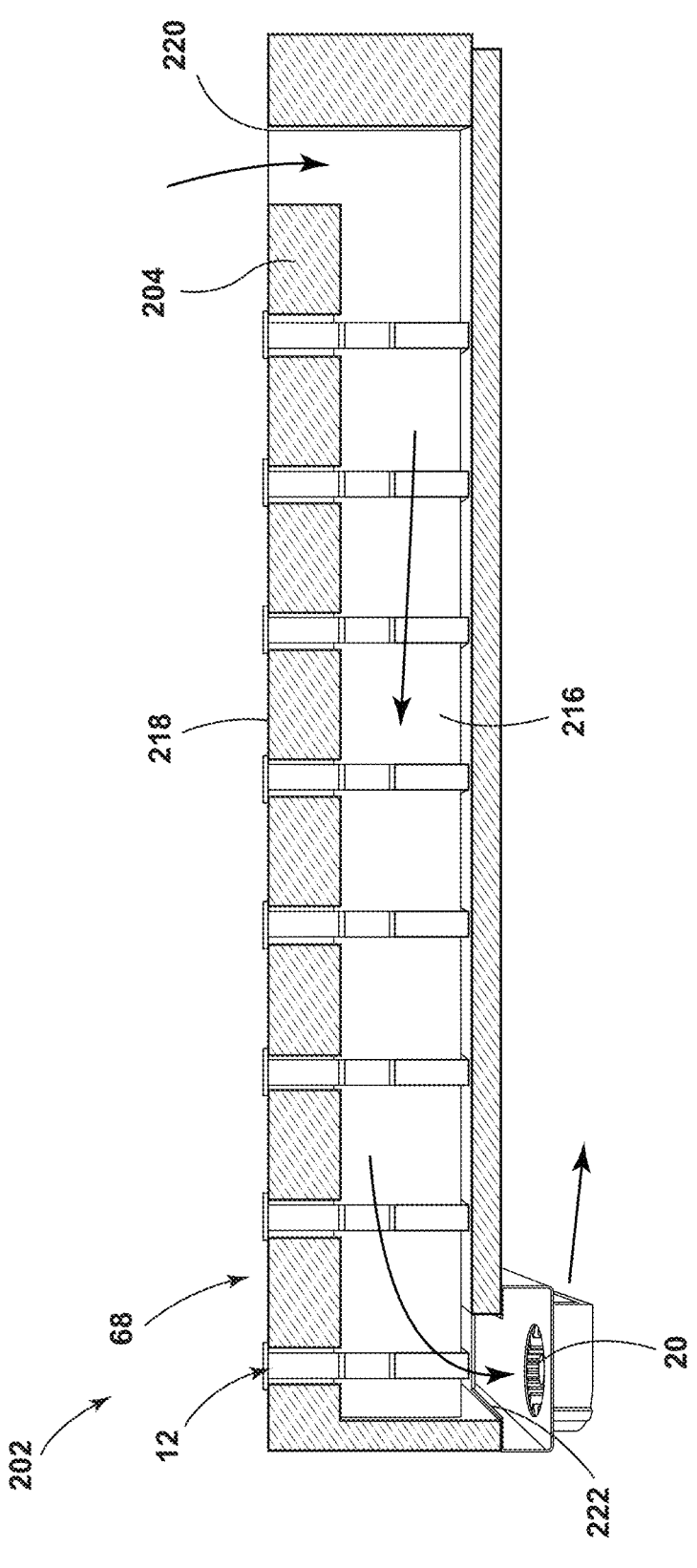
FIG. 11 is a side elevational cross-sectional view of a thermoelectric module with a thermoelectric device and a fan, according to the present disclosure.

Referring to FIGS. 10 and 11, the thermoelectric device 12 may have an elongated configuration. The thermoelectric device 12 may include multiple p- and n-semiconductors 206, 208, which are configured to generate heat flux across junctions 210. The temperature difference generated through the Peltier effect is generally created by transferring heat between two junctions 210. The semiconductors 206, 208 may be arranged in an alternating pattern and coupled via electrical connectors 212. The thermoelectric device 12 may include any practicable number of semiconductors 206, 208, junctions 210, and electrical connectors 212. The thermoelectric device 12 may form an elongated feature extending along or through the support structure 204. In certain aspects, the thermoelectric device 12 may form a pattern, such as a serpentine pattern across the support structure 204.

The thermoelectric device 12 disclosed herein operates via the Peltier effect. When a voltage is applied to the semiconductors 206, 208 to direct a current in a first direction, the first side 84 of the thermoelectric device 12 is the cold side while the second side 86 is the heated side. When the current is directed in an opposing direction, the first side 84 is heated and the second side 86 is cold. The thermoelectric device 12 is operably coupled to a power source 214 for providing the voltage to the thermoelectric device 12 to generate the heat flux. The changing of the heated and cooled sides 84, 86 may be advantageous for heating and cooling areas 24, 26 of the patient with the same thermoelectric module 202.

The support structure 204 defines an airflow channel 216 for directing air past the thermoelectric device 12 and moving the heated or cooled air out of the thermoelectric module 202. The second side 86 of the thermoelectric device 12 is generally positioned within the airflow channel 216 while the first side 84 of the thermoelectric device 12 is arranged proximate to a top 218 of the support structure 204. The top 218 is oriented toward the patient. In this way, the temperature of the first side 84 produces the temperature effect felt by the patient while the temperature effect from the second side 86 is directed away from the patient by the fan 20.

The support structure 204 is generally constructed of foam or a similar material. In certain aspects, the top 218 is constructed of a different material than the bottom or is constructed of a material having different properties. In such examples, the top 218 of the support structure 204 may provide cushioning and support to the patient, while an area defining the airflow channel 216 is more rigid to retain its structure under the weight of the patient.

Referring still to FIGS. 10 and 11, the support structure 204 defines an inlet 220 to allow the air to be drawn away from the patient and into the airflow channel 216. The fan 20 is disposed proximate to an outlet 222 on the opposing side of the support structure 204. Generally, the fan 20 draws air through the inlet 220, through the airflow channel 216, which draws air past the second side 86 of the thermoelectric device 12, and through the outlet 222. For example, when the first side 84 provides the cooling temperature effect, the second side 86 provides the warming temperature effect. The air is drawn through the airflow channel 216 to draw the heat generated by the thermoelectric device 12 away from the patient, which also assists the thermoelectric device 12 in continuing to operate efficiently.

Figure 12:
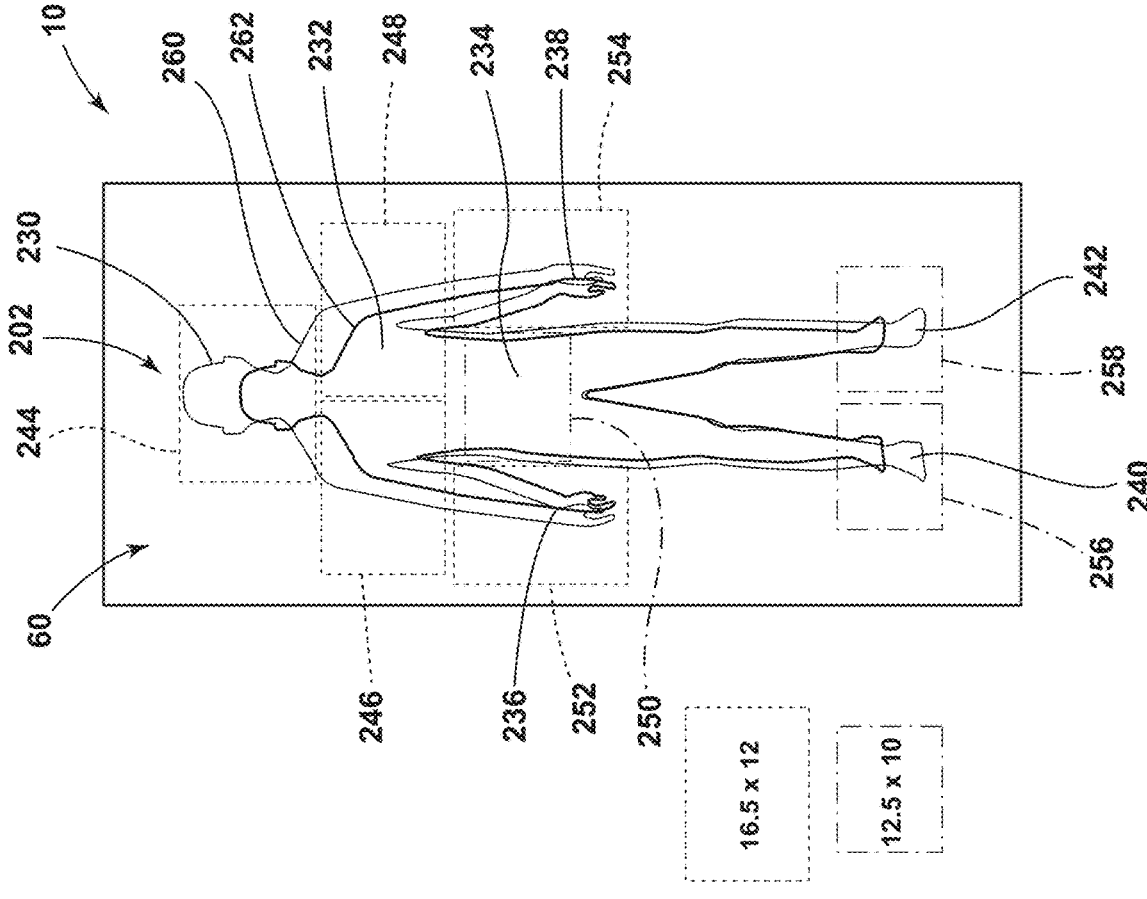
FIG. 12 is representative of a heat exchange system having multiple thermoelectric modules positioned relative to patients, according to the present disclosure.

Referring to FIG. 12, the thermoelectric modules 202 are self-contained units that provide for flexibility in the care and treatment of the patient on the bed 180. The thermoelectric modules 202 may be arranged in a variety of configurations based on the treatment to be provided to the patient. The thermoelectric modules 202 may be disposed in predefined locations in the support surface assembly 60. In such examples, different support surface assemblies 60 may be interchanged with one another to provide the heat exchange system 10 with the selected configuration of the thermoelectric modules 202. Alternatively, the caregiver may reposition the core blocks 200 to insert or remove the thermoelectric modules 202 to provide the selected configuration of the heat exchange system 10.

As illustrated in FIG. 12, the heat exchange system 10 may be utilized to affect the temperature between one and five different areas (e.g., the cooled first areas 24 and the heated second areas 26) on the patient. These areas include a head region 230, a chest region 232, a sacral region 234, upper extremity regions 236, 238, and lower extremity regions 240, 242. To cover each of these regions, the heat exchange system 10 may include up to eight thermoelectric modules 244-258, which are collectively referred to herein as the thermoelectric modules 202. One thermoelectric module 244 is positioned to align with the head region 230. Two thermoelectric modules 246, 248 are disposed side-by-side to align with the chest region 232. One thermoelectric modules 250 may align with the sacral region 234. Further, one thermoelectric module 252, 254 may align with each of the upper extremity regions 236, 238, respectively. Additionally, the thermoelectric modules 256, 258 may align with the lower extremity regions 240, 242, respectively.

In certain aspects, one, several, or all eight thermoelectric modules 202 may be included in the heat exchange system 10. The number and arrangement of the thermoelectric modules 202 may depend on the treatment and therapy provided to the patient. Further, the heat exchange system 10 may be arranged to align with the selected bony prominences on each of a male patient 260 and a female patient 262. The controller 22 may store patient anthropometry to be used to determine the selected bony prominences and an estimated position thereof. Further, the selected patient anthropometry may be utilized to determine the positions of the thermoelectric modules 202 to align with the bony prominences. The locations of the thermoelectric modules 202 are illustrated to align with a 95th percentile male patient 260 and a fifth percentile female patient 262. The stored information may be standardized information or customized for the patient. Additionally, the controller 22 may be configured to determine the location of the bony prominences with sensed information as described further herein.

Referring still to FIG. 12, as previously stated, the thermoelectric modules 202 may be different sizes depending on the location the thermoelectric module 202 is positioned relative to the patient. For example, smaller thermoelectric modules 202 may align with the sacral region 234 and the lower extremity regions 240, 242 while larger thermoelectric modules 202 align the head region 230, the chest region 232, and the upper extremity regions 236, 238. The difference in sizes may be based on spacing in the support surface assembly 60, the size of the bony prominence area, and/or other factors.

Figure 13:
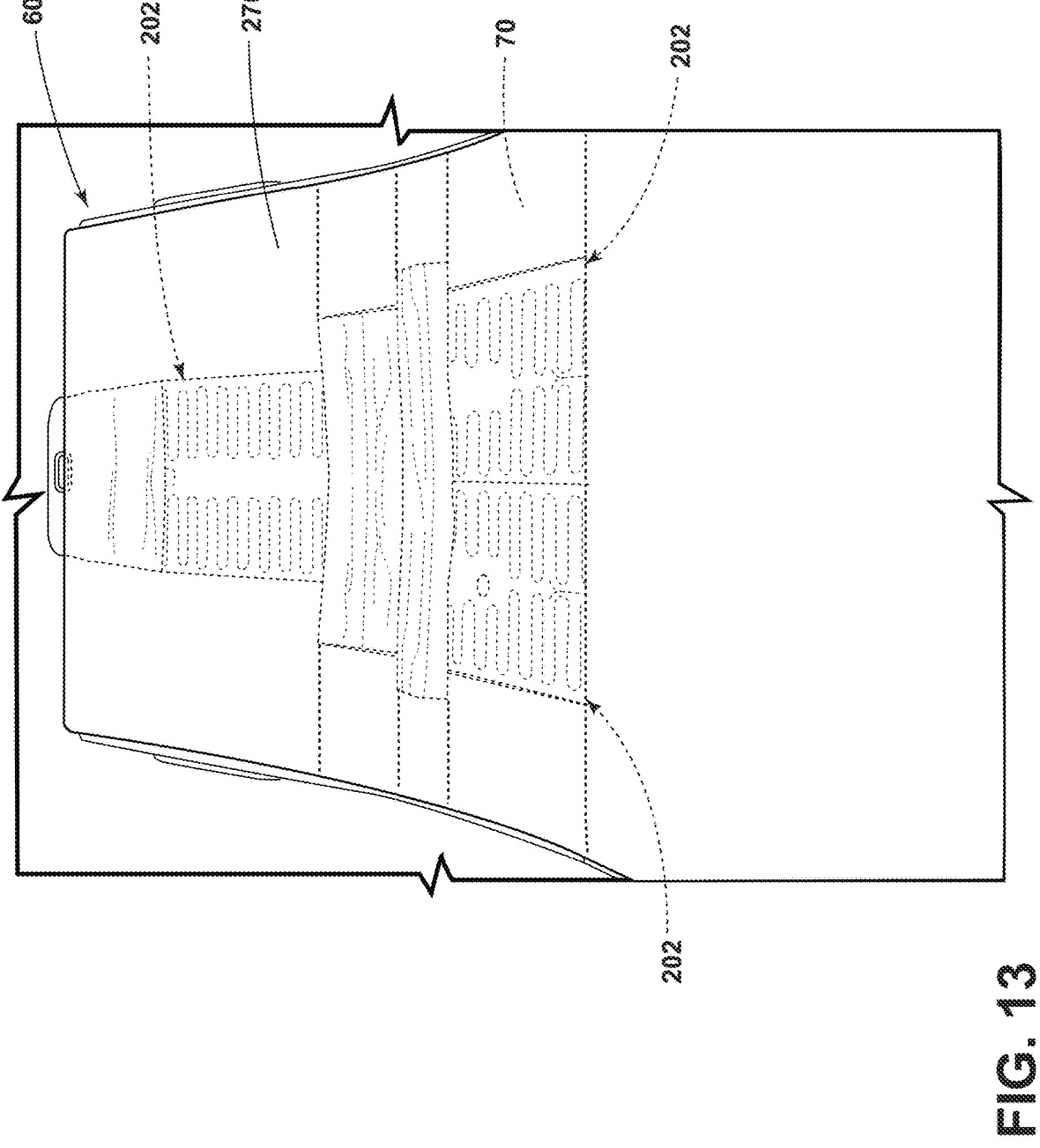
FIG. 13 is a partial top perspective view of a topper positioned on a support surface assembly having a heat exchange system, according to the present disclosure.
Figure 14:
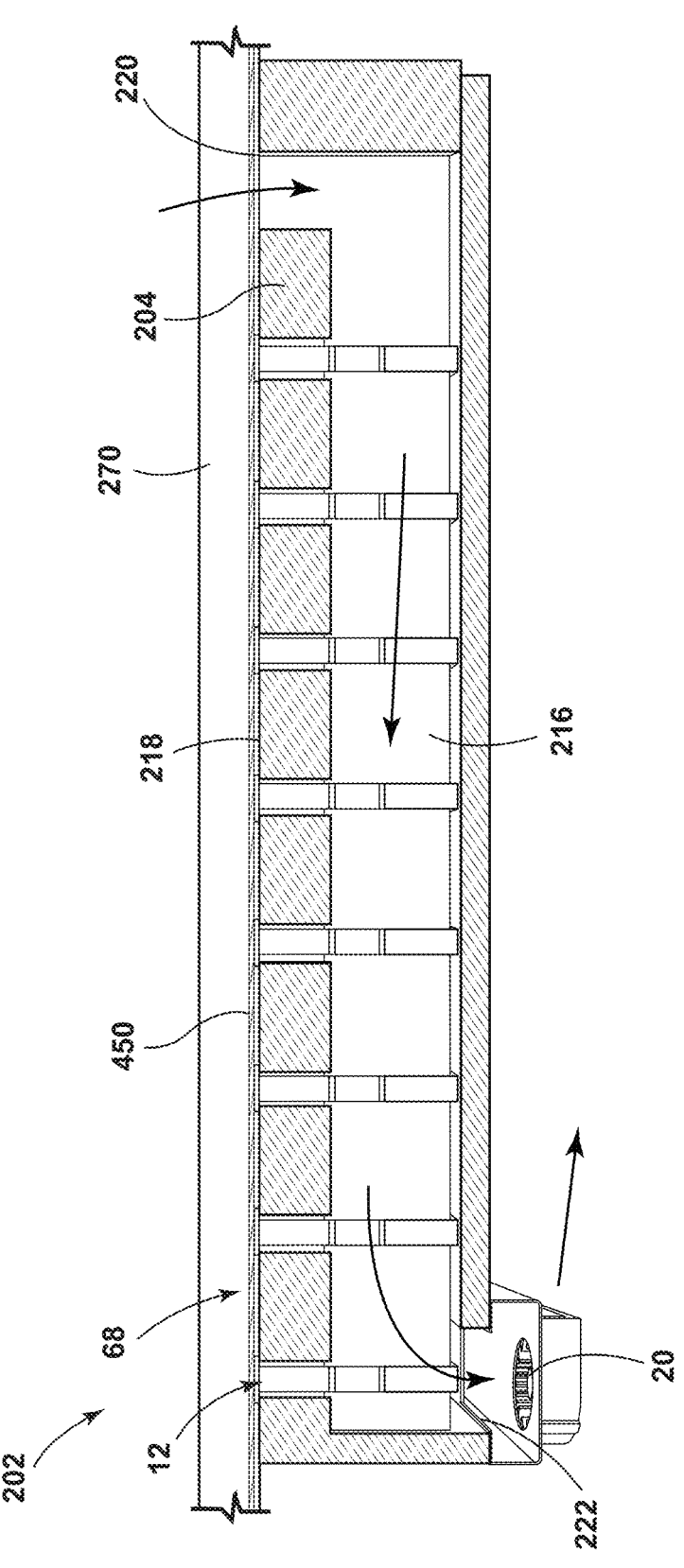
FIG. 14 is a side elevational cross-sectional view of a topper positioned on a thermoelectric module with a thermoelectric device and a fan, according to the present disclosure.

Referring to FIGS. 13 and 14, the heat exchange system 10 may include a topper 270 positioned over the thermoelectric modules 202 and/or the core blocks 200. The topper 270 may be disposed on the top surface 82 of the outer ticking 72 or may be disposed within the outer ticking 72 and over the core blocks 200 and the thermoelectric modules 202. The topper 270 may be constructed of a conductive material allowing the temperature effects from the thermoelectric modules 202 to be transferred to the patient through the topper 270. In such examples, the topper 270 may provide increased comfort to the patient by providing an increased cushion between the patient and the thermoelectric modules 202.

Additionally or alternatively, the topper 270 may be the MCM system. The MCM system generally includes a blower, a top coverlet, and a spacer material within the top coverlet. The blower operates to direct or blow air through the spacer material. While the patient is positioned on the MCM system, the air is directed through the top coverlet. This configuration wicks away moisture from the skin of the patient by blowing air beneath the patient, which is advantageous for preventing skin conditions that may be caused by lying on the mattress for an extended period of time. The air traveling through the top coverlet may be utilized to cool or warm the patient based on the operation of the thermoelectric device 12.

Figure 15:
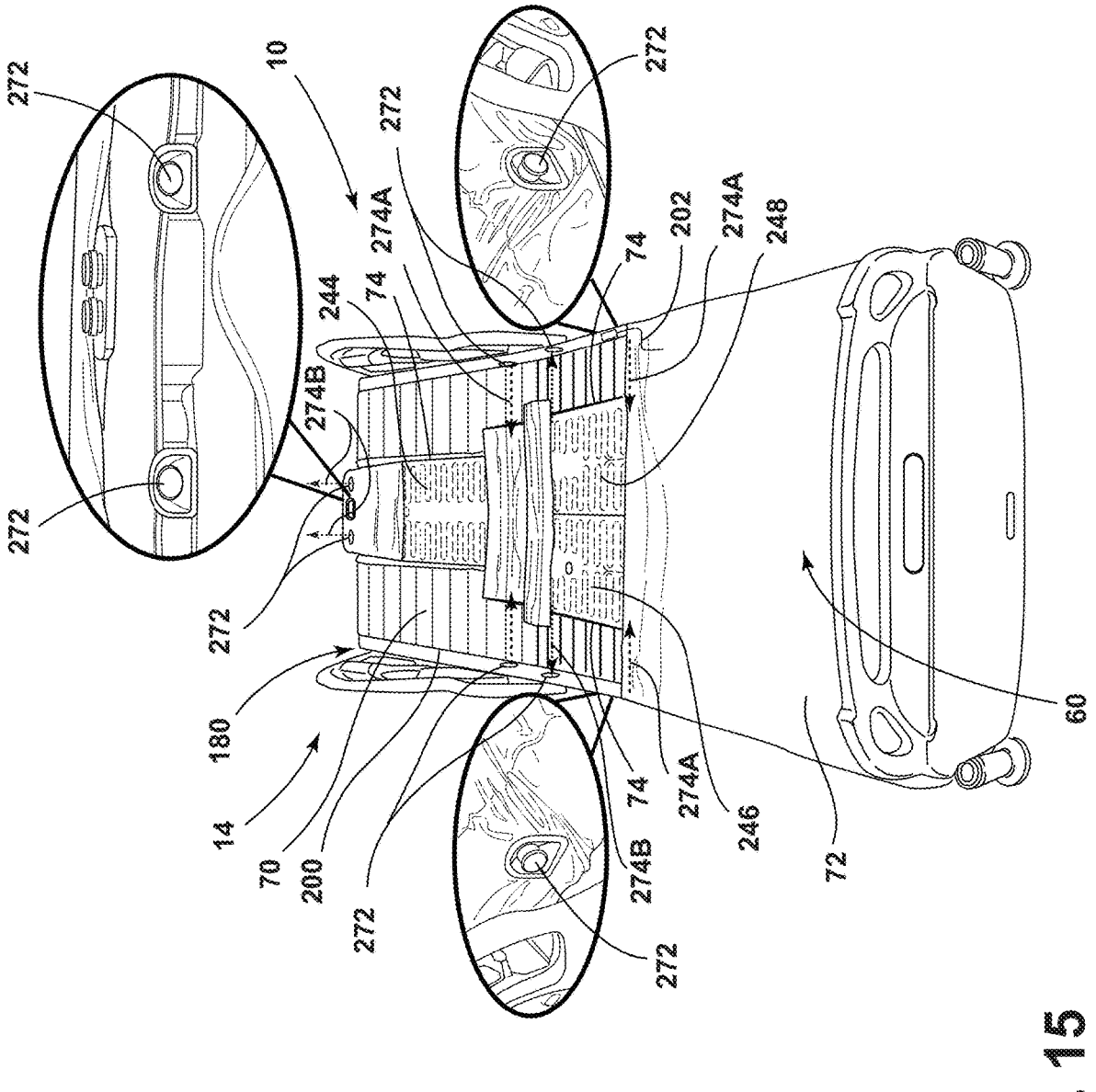
FIG. 15 is a top perspective view of an interior of a support surface assembly on a medical bed, illustrating airflow due to thermoelectric modules, according to the present disclosure.
Figure 16:
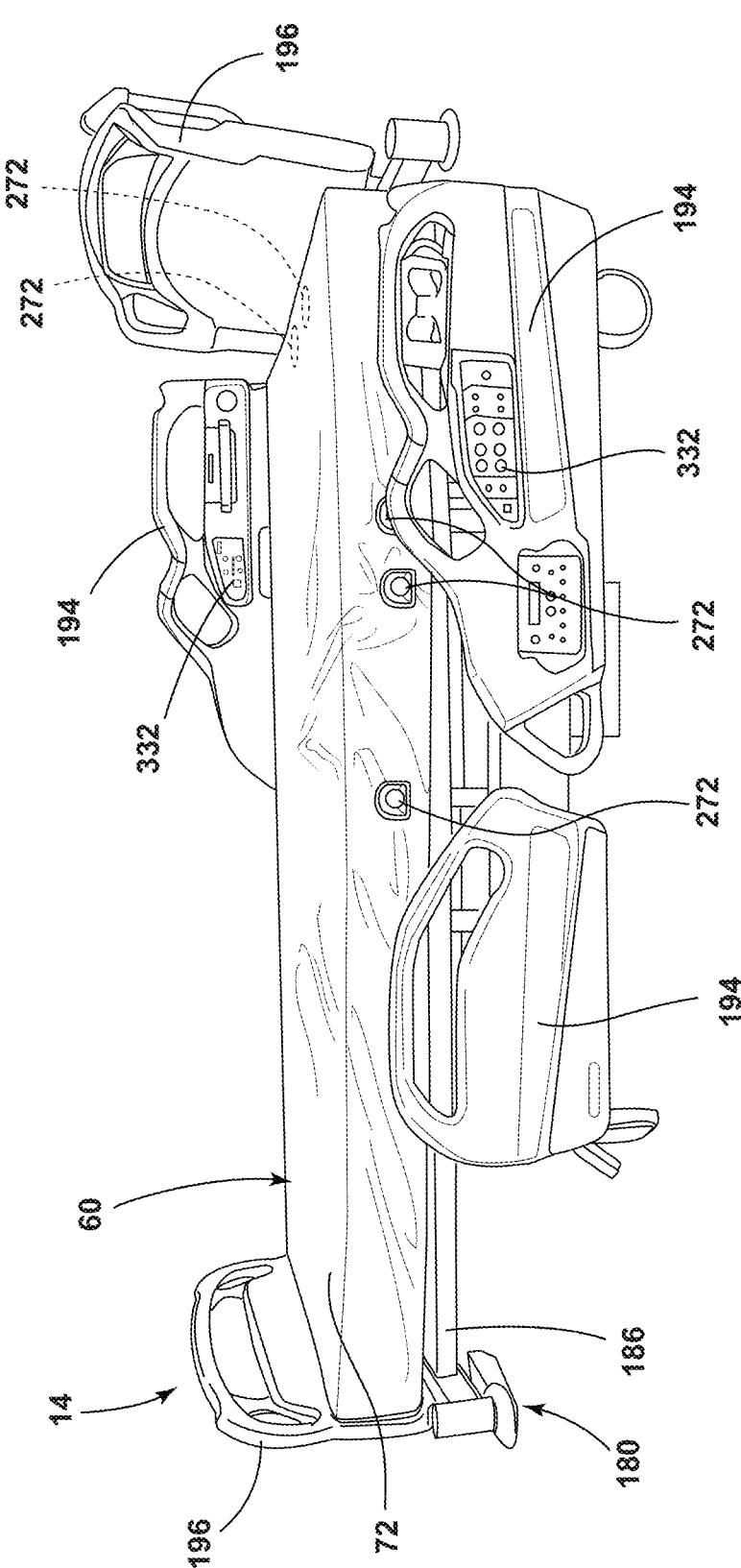
FIG. 16 is a side plan view of a bed with vents in an outer ticking of the support surface assembly, according to the present disclosure.
Figure 17:
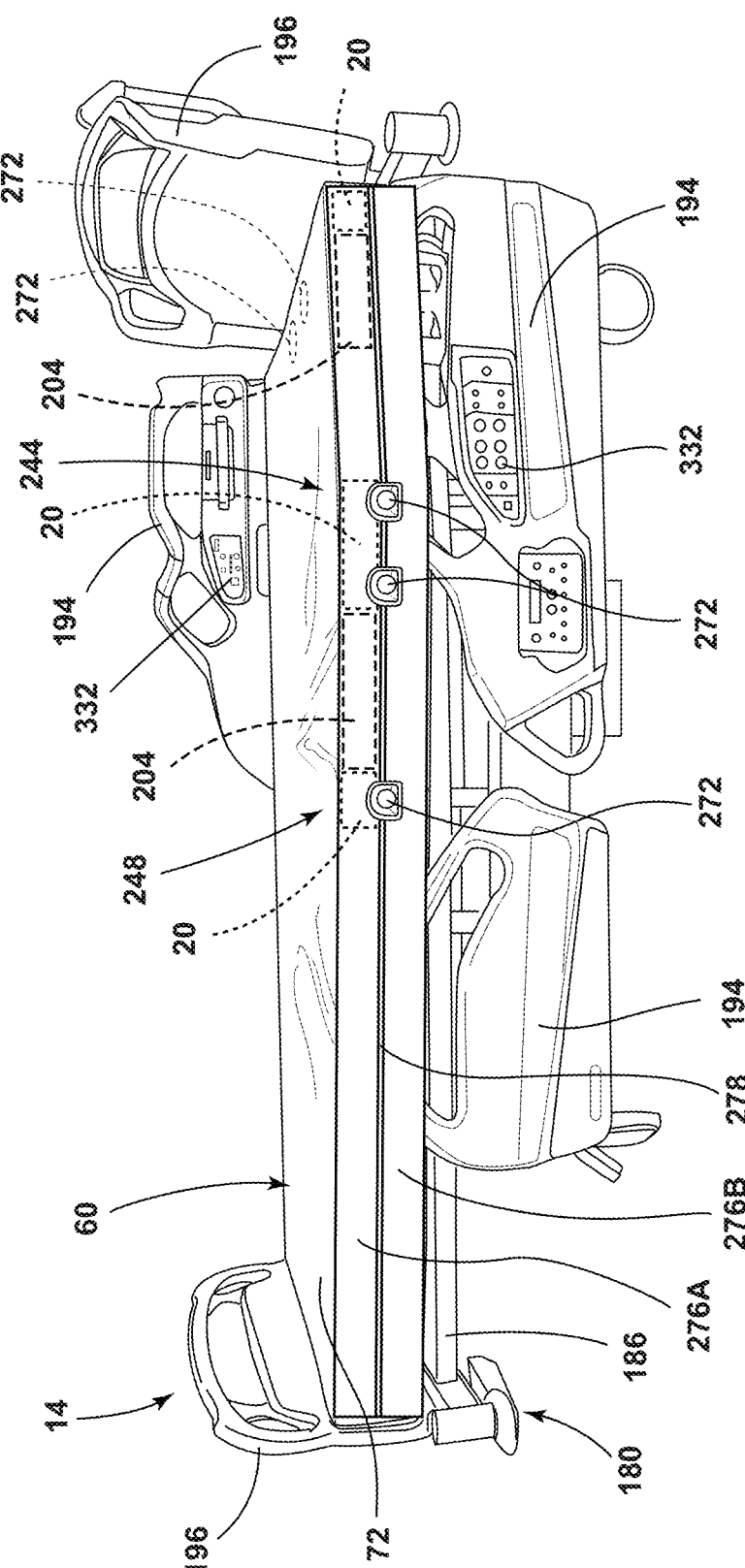
FIG. 17 is a side plan view of an interior of a support surface assembly having thermoelectric modules aligned with vents in an outer ticking, according to the present disclosure.

Referring to FIGS. 15-17, an exemplary configuration of the heat exchange system 10 is illustrated on the bed 180. The support surface assembly 60 is disposed on the upper frame 186 of the bed 180. The support surface assembly 60 includes the core 70 constructed of the core blocks 200. The illustrated example includes the thermoelectric module 244 configured to align with a back region of the patient and the thermoelectric modules 246, 248 configured to align with a seat region of the patient.

The support surface assembly 60 includes multiple vents 272 around the outer ticking 72, which are configured to align with the thermoelectric modules 244, 246, 248. The thermoelectric modules 244, 246, 248 are configured to draw cool air, illustrated by arrows 274A, across the core blocks 200 and the support structures 204. The thermoelectric modules 244, 246, 248 are also configured to direct warm or heated air, illustrated by arrows 274B, through the vents 272 and out of the support surface assembly 60. Alternatively, the air vented out of the support surface assembly 60 may be cool air when the heat exchange system 10 is warming the patient. In another non-limiting example, some of the thermoelectric modules 202 may heat the patient, while others cool the patient. The inlet 220 and the outlet 222 defined by the support structures 204 of the thermoelectric modules 202 may be positioned in any practicable position on the support structure 204 to drive the selected airflow pattern represented by the arrows 274A, 274B.

In the illustrated example, three vents 272 are disposed on a first lateral side of the support surface assembly 60 and three vents 272 on a second lateral side of the support surface assembly 60. Further, two vents 272 are disposed on a head edge of the support surface assembly 60. The multiple vents 272 allow the heated air to be directed away from the patient. Additional vents 272 may be included in the support surface assembly 60 to provide increased flexibility for the heat exchange system 10.

As illustrated in FIG. 17, the core 70 includes two layers 276A, 276B of core blocks 200. The thermoelectric modules 244, 246, 248 are disposed within the cavities 74 of the first layer 276A. A spacer 278 is positioned between and separates the two layers 276A, 276B of the core 70. The spacer 278 is air permeable and provides for airflow within the support surface assembly 60. The vents 272 are aligned with the spacer 278, allowing the air to be directed through the spacer 278 and out of the vents 272.

The support structures 204 with the thermoelectric devices 12 are positioned in the first layer 276A of the core 70. The bed 180 includes multiple fans 20. In the illustrated example, at least one fan 20 is positioned on each opposing side (e.g., a head side and a foot side) of the support structures 204 for the thermoelectric modules 246, 248, and at least one fan 20 is positioned adjacent to the headboard 196 and the thermoelectric module 244. In various examples, there may be the same number of fans 20 and vents 272. Alternatively, there may be the same number of fans 20 and thermoelectric devices 12. The fans 20 operate to direct air through the support structures 204 and/or through the spacer 278. The fans 20 also operate to drive the warm air through the vents 272. This configuration of the heat exchange system 10 is merely exemplary and may be adjusted based on the number and location of the thermoelectric modules 202 utilized within the support apparatus 14.

In the illustrated example, the thermoelectric module 244 may produce a first temperature effect, such as a heating or warming effect, while the other thermoelectric modules 246, 248 produce a second temperature effect, such as a cooling effect. The heat exchange system 10 directs the current in the first direction through the thermoelectric device 12 in the thermoelectric module 244 to produce the warming effect and directs the current in the second direction through the thermoelectric devices 12 of the thermoelectric modules 246, 248 to produce the cooling effect. The heat exchange system 10 may receive a user input from the patient or caregiver relating to one, some, or all of the thermoelectric modules 202 in the heat exchange system 10 and may selectively and independent control the thermoelectric modules 202 in accordance with the user inputs.

Figure 19:
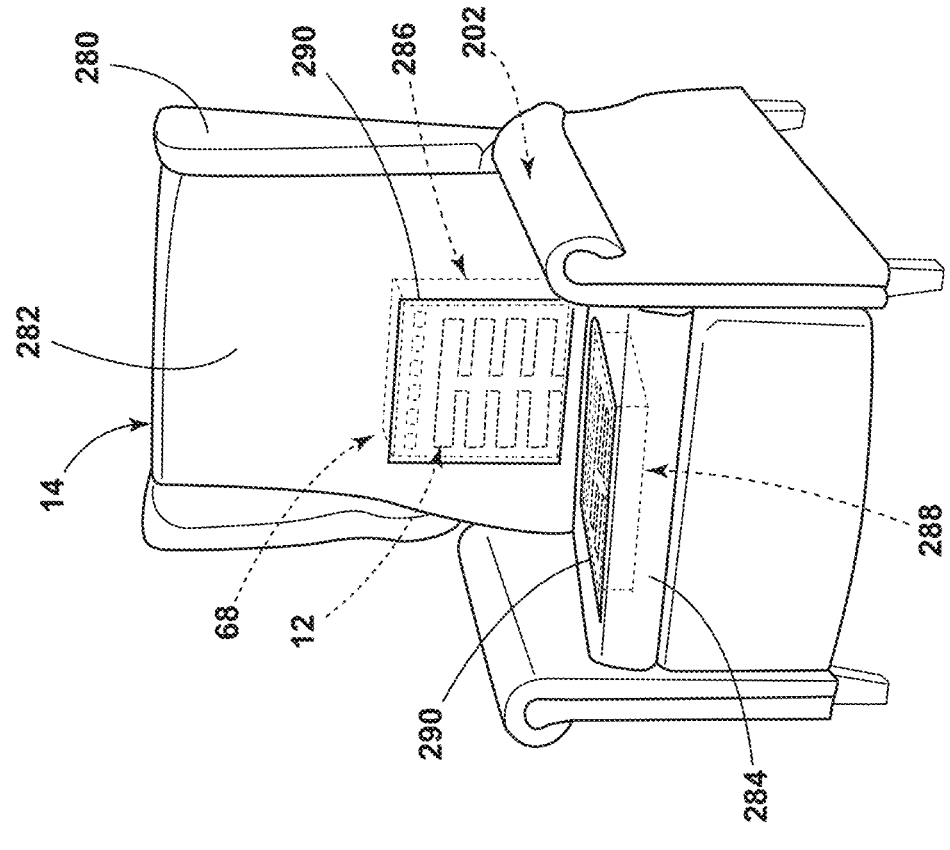
FIG. 19 is a front perspective view of a patient chair having thermoelectric modules of a heat exchange system, according to the present disclosure.
Figure 18:
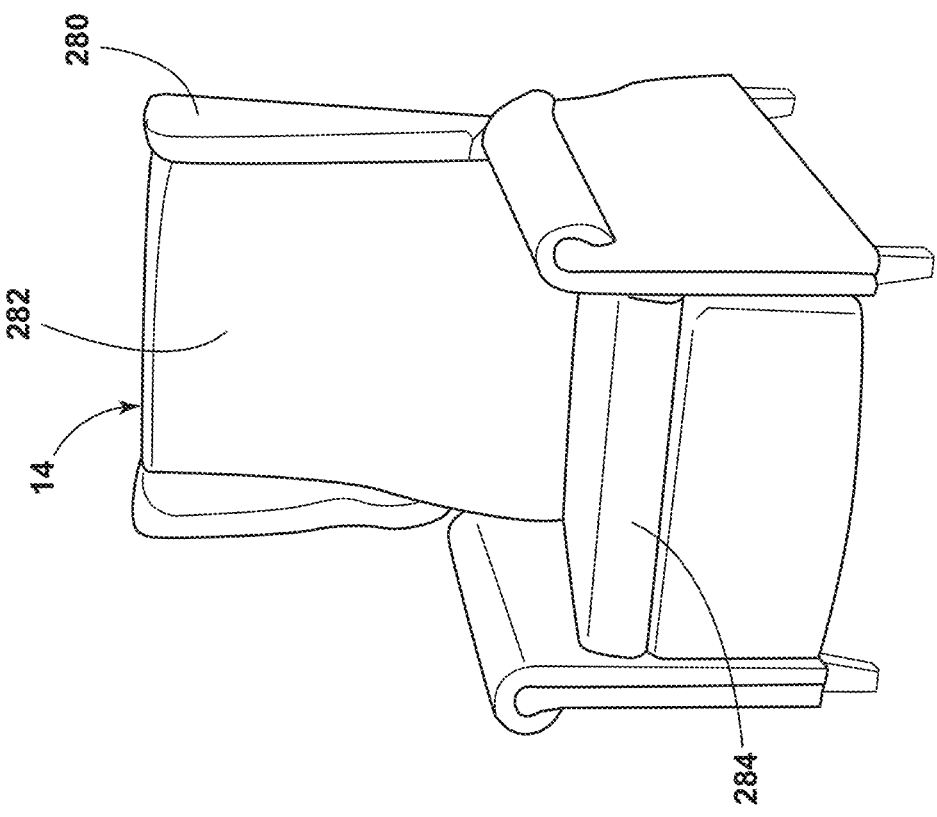
FIG. 18 is a front perspective view of a chair for a patient, according to the present disclosure.

Referring to FIGS. 18 and 19, the patient may be positioned at or on different types or configurations of support apparatuses 14 during his or her stay at the medical facility. For example, some patient rooms 182 may include a chair 280 (e.g., a configuration of the support apparatus 14), and the heat exchange system 10 may be utilized with the chair 280. The chair 280 includes a seatback 282 and a seat base 284. The seatback 282 may be adjustable relative to the seat base 284. The chair 280 may be configured to include the thermoelectric modules 202 in one or both of the seatback 282 and the seat base 284.

In the example illustrated in FIG. 19, two thermoelectric modules 286, 288, collectively referred to herein as the thermoelectric modules 202, are included in the chair 280. One thermoelectric module 286 is positioned in the seatback 282 and the other thermoelectric module 288 is in the seat base 284. A covering 290 may be disposed over the thermoelectric modules 202 to obscure the thermoelectric modules 202 from view. Additionally, the covering 290 may include support or cushioning for reducing the feel of the thermoelectric modules 202 when the patient is positioned on the chair 280.

Referring to FIGS. 8-19, each thermoelectric module 202 is selectively and independently operable. For example, one thermoelectric module 202 at the first location 16 may operate to cool the first area 24 of the patient, while another thermoelectric module 202 at the second location 18 may operate to heat the second area 26 on the patient at the same time. The thermoelectric modules 202 may each operate to heat or cool the corresponding area of the patient based on therapy, treatment, or comfort. The thermoelectric modules 202 may be used to form independent heating and cooling zones in the support surface assembly 60. The thermoelectric modules 202 may reduce or eliminate the use of accessories, which may be cumbersome, utilize caregiver time to retrieve, and can utilize space around the patient.

At least one of the controller 22 and the heat exchange system 10 may include software (e.g., logic or routines) for controlling the fans 20 based on the cooling effect provided to the patient. The software may include rules-based logic to determine how much thermoelectric cooling is occurring via the thermoelectric device 12. In various examples, the rules-based logic may be utilized for determining the current applied to the thermoelectric devices 12, an amount of time the current has been applied to the thermoelectric devices 12, a position of the thermoelectric modules 202 relative to the patient, etc. After determining the amount of thermoelectric cooling, a speed of the fan 20 may be controlled to control the temperature effect felt by the patient.

Further, the configurations of the heat exchange system 10 with the thermoelectric modules 202 may include the temperature sensor 174. The temperature sensor 174 is generally positioned within the support surface assembly 60 or the support apparatus 14 and may sense the temperature proximate to the thermoelectric modules 202. The speed of the fans 20 may be adjusted in response to the temperature sensed by the temperature sensor 174. The heat exchange system 10 may utilize any practicable number of temperature sensors 174 without departing from the teachings herein. The fans 20 may be controlled to affect the temperature sensed by the temperature sensors 174 and, consequently, the temperature effects felt by the patient. Controlling the speed of the fans 20 by software and/or the sensed temperature may be advantageous to control noise generated by the heat exchange system 10, prolong service life of the heat exchange system 10, and control the temperature effect felt by the patient.

Referring to FIGS. 1-19, the configurations of the heat exchange system 10 may be used on multiple types of support apparatuses 14. The various types of support apparatuses 14 include the surgical or operating table 42, the bed 180, the chair 280, stretchers, birthing beds, intensive care unit and surgical beds, homecare platforms, patient covers, patient gowns, compression boots, etc. Additionally, the heat exchange system 10 may be integrated into the support apparatus 14 or may be a separate assembly that may be coupled to and used with the support apparatus 14.

Further, it is contemplated that the different configurations of the heat exchange system 10 may be utilized in different configurations of the support apparatus 14 other than those illustrated. For example, the configurations of the heat exchange system 10 illustrated with the operating table 42 in FIGS. 1-7 may be used with the bed 180, the chair 280, or other support apparatuses 14. Additionally, the configurations of the heat exchange system 10 illustrated with the bed 180 in FIGS. 8-17 may be used with the operating table 42, the chair 280, or other support apparatuses 14. Further, the configuration of the heat exchange system 10 illustrated with the chair 280 in FIGS. 18 and 19 may be used with the operating table 42, the bed 180, and other support apparatuses 14.

Additionally, while the support surface assembly 60 is generally described herein as having a core 70 of foam materials, it is contemplated that the support surface assembly 60 and/or the core 70 may have other configurations and still be used with the heat exchange system 10. For example, the support surface assembly 60 may be an air surface or a pulmonary surface without departing from the teachings herein. In such examples, the heat exchange system 10 may be coupled with the support surface assembly 60 to provide multiple therapies to the patient.

Figure 20:
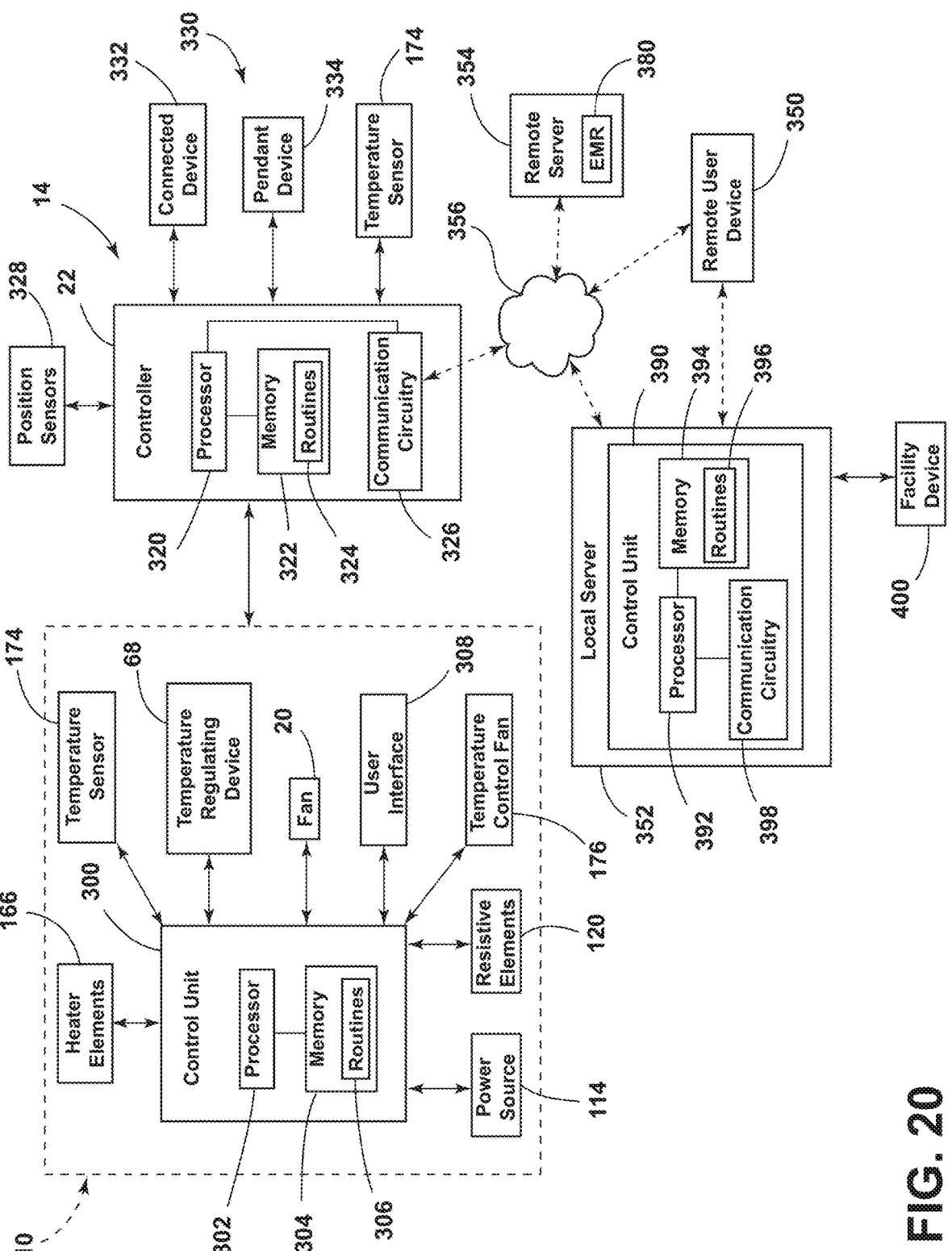
FIG. 20 is a block diagram of a medical facility with multiple systems in communication via a communication interface, according to the present disclosure.

Referring to FIG. 20, the heat exchange system 10 includes a control unit 300 having a processor 302, a memory 304, and other control circuitry. Instructions or routines 306 are stored within the memory 304 and executable by the processor 302. As the heat exchange system 10 may be a separate assembly, the heat exchange system 10 may include a user interface 308 for activating various aspects of the heat exchange system 10. The control unit 300 is in communication with the various components of the heat exchange system 10, including at least one of the temperature regulating device 68 (e.g., the thermoelectric device 12, the compressor 160, and/or the thermoelectric module 202), the fan 20, the resistive elements 120, the heater element 168, the temperature control fan 176, the power source 214, and the user interface 308. In response to an input from the user interface 308, the control unit 300 may activate one or more of the various components of the heat exchange system 10.

Additionally or alternatively, the control unit 300 is in communication with the controller 22 of the support apparatus 14, such that the support apparatus 14 may be utilized to control the heat exchange system 10. The controller 22 includes a processor 320, a memory 322, and other control circuitry. Instructions or routines 324 are stored within the memory 322 executable by the processor 320. The control circuitry may also include communication circuitry 326 configured for bidirectional wireless and wired communications.

The heat exchange system 10 may be arranged to align with the selected bony prominences of the patient. However, the position of the patient may change based on the position of the support apparatus 14, the movement of the patient, etc. The support apparatus 14 may include position sensors 328 configured for monitoring a position of the patient on the support apparatus 14. The position sensors 328 may be configured as force or weight sensors, optical cameras, load cells, pressure sensors, strain gauges, a pressure sensing mat, etc. The position sensors 328 may sense the position or the change in position of the patient.

For example, when the support apparatus 14 is the bed 180 and the segment 188 is adjusted to elevate the head of the patient, the patient may slide slightly along a longitudinal extent of the bed 180 toward the footboard 198. In another non-limiting example, the patient may turn to his or her side. The position sensors 328 may sense the new position of the patient and communicate position information to the controller 22.

The sensed position information and any estimation in position determined by the controller 22 may be utilized to control the heat exchange system 10. Estimated positions may utilize the sensed position information and the stored patient anthropometry. The sensed position information may be used in conjunction with the known or stored patient anthropometry to control the thermoelectric modules 202. For example, the position of the patient may be utilized for activating various aspects of the heat exchange system 10 based on the position of the patient (e.g., the position information). In this way, the selected locations for heating and cooling may be adjusted based on the position of the patient to provide increased treatment and a greater therapeutic effect. In another non-limiting example, the controller 22 may utilize the sensed position information to monitor the movement of the patient. If the movement of the patient exceeds a predefined threshold, the cooling by the heat exchange system 10 may be reduced or deactivated. In such examples, the movement may be determined to be sufficient for reducing pressure injury development.

The support apparatus 14 also includes a user interface assembly 330 for receiving inputs from the patient or the caregiver with respect to the support apparatus 14. The inputs may relate to the position of the support apparatus 14 or control of the heat exchange system 10. For example, when the support apparatus 14 is the bed 180, the user interface assembly 330 includes a connected device 332, which may include a handheld control, buttons, or a graphical user interface connected to the bed 180, such as on the side rails 194. Additionally, the user interface assembly 330 may include a pendant device 334 that may be coupled with the bed 180 (see FIG. 8). The pendant device 334 may be selectively coupled with the bed 180 by a rod 336. The pendant device 334 is typically suspended in front of the patient for the patient to view while on the bed 180.

Referring still to FIG. 20, the patient and the caregiver may control the heat exchange system 10 through the user interface assembly 330 on the support apparatus 14. In such examples, the user input may be communicated to the controller 22, and the controller 22 may communicate the user input to the control unit 300 of the heat exchange system 10. Generally, the user inputs relating to heat exchange system 10 may include activation, deactivation, increase in temperature, decrease in temperature, setting temperature ranges, locking controls, etc. Typically, the heat exchange system 10 is physically coupled with the support apparatus 14 to be in communication with the controller 22, but the controller 22 and the control unit 300 may also be configured for wireless communication.

The controller 22 of the support apparatus of 14 may also be in communication with various remote features, such as a remote user device 350, a local server 352, and a remote server 354 via a communication network 356. The communication network 356 may be part of a network of the medical facility, which may include a combination of wired connections (e.g., Ethernet 358), as well as wireless connections, which may include the wireless communication network 356. The communication network 356 may include a variety of electronic devices, which may be configured to communicate over various wired or wireless communication protocols. The communication network 356 may include a wireless router through which the remotely accessed devices may be in communication with one another as well as the local server 352. Additionally, remotely accessed devices, such as the remote user device 350, may communicate directly with the local server 352.

The communication network 356 may be implanted via one or more direct or indirect nonhierarchical communication protocols, including but not limited to, Bluetooth®, Bluetooth® low energy (BLE), Thread, Ultra-Wideband, Z-wave, ZigBee, etc. Additionally, the communication network 356 may correspond to a centralized or hierarchal communication network 356 where one or more of the devices communicate via the wireless router (e.g., a communication routing controller). Accordingly, the communication network 356 may be implemented by a variety of communication protocols, including, but not limited to, global system for mobile communication (GSM), general packet radio services, code division multiple access, enhanced data GSM environment, fourth generation (4G) wireless, fifth generation (5G) wireless, Wi-Fi, world interoperability for wired microwave access (WiMAX), local area network, Ethernet 358, etc. By flexibly implementing the communication network 356, the various devices and servers may be in communication with one another directly via the wireless communication network 356, or cellular data connection.

Figure 21:
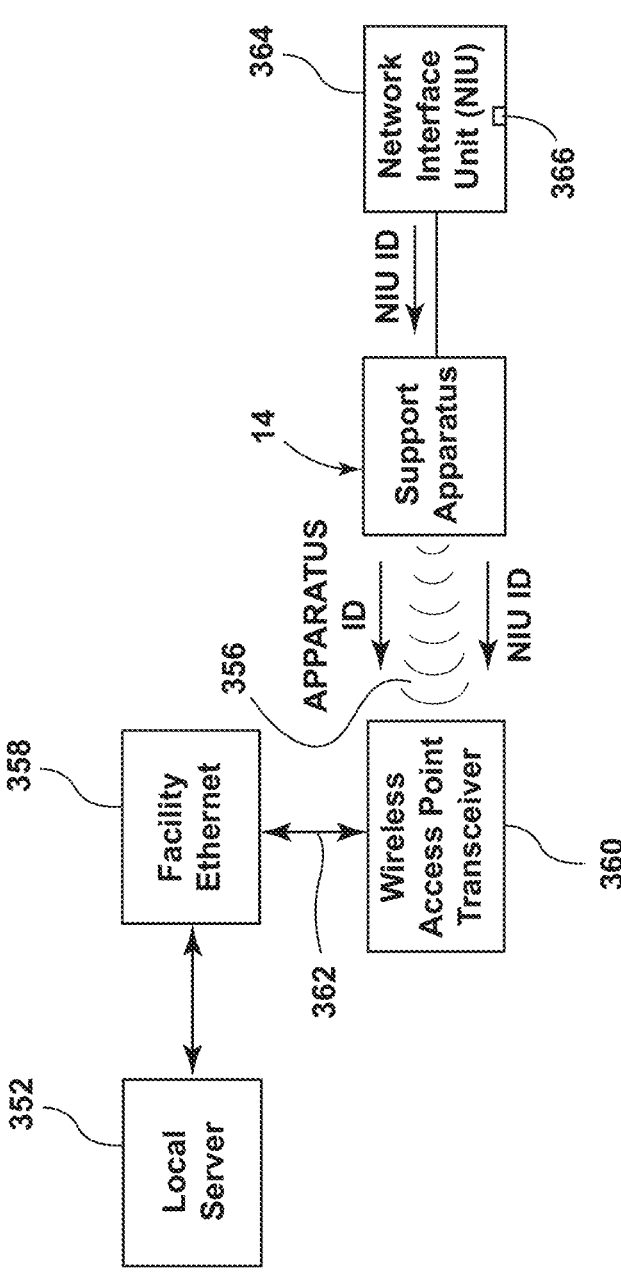
FIG. 21 is a block diagram of a support apparatus wirelessly communicating with a local server via a wireless access transceiver, according to the present disclosure.
Figure 22:
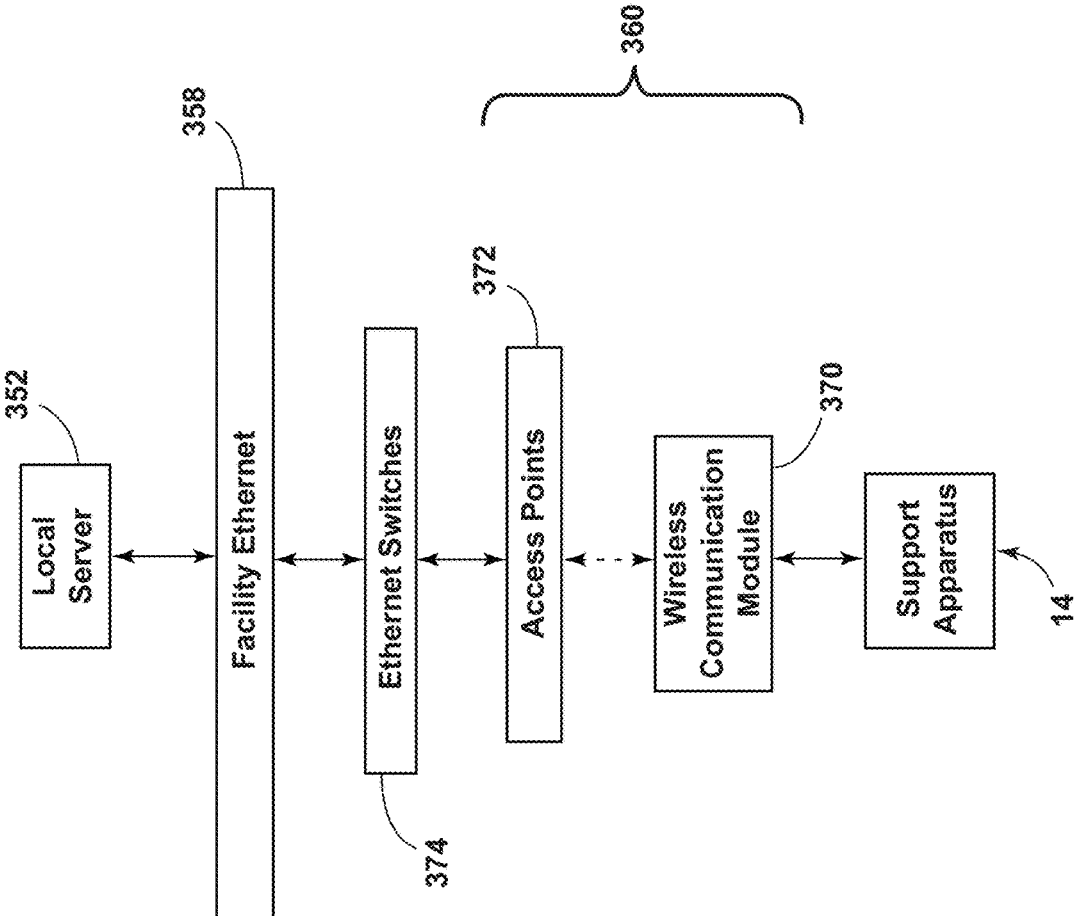
FIG. 22 is a block diagram of treatment devices wirelessly communicating with a local server via wireless access points, according to the present disclosure.

Referring still to FIG. 20, as well as to FIGS. 21 and 22, exemplary communications methods between the support apparatus 14 and the local server 352 are illustrated. In certain aspects, the support apparatus 14 is configured to communicate with a wireless access transceiver 360, which is coupled to Ethernet 358 of the medical facility. The communication network 356 provides for bidirectional communication between the support apparatus 14 and the wireless access transceiver 360. The wireless access transceiver 360 communicates bidirectionally with Ethernet 358 via a datalink 362

As illustrated in FIG. 21, the support apparatus 14 may be associated with a network interface unit 364. Multiple network interface units 364 may be provided in various locations of the medical facility. Each support apparatus 14 and each network interface unit 364 is assigned a new identification code such as a serial number. Various components of the local server 352 may include software that operates to associate the identification code of the support apparatus 14 with the network interface unit identification data to locate each support apparatus 14 in the medical facility. Each network interface unit 364 includes a port 366 for selectively coupling with Ethernet 358. The network interface unit 364 is coupled with Ethernet 358. The network interface unit 364 communicates identification data to the support apparatus 14, which then wirelessly communicates the data to the support for the support apparatus 14 and the network interface unit 364 to the wireless access transceiver 360. The wireless access transceiver 360 communicates with the local server 352 via Ethernet 358.

As illustrated in FIG. 22, the support apparatus 14 may be capable of communicating wirelessly via a wireless communication module 370. The wireless communication module 370 generally communicates via an SPI link with circuitry associated with the support apparatus 14 (e.g., the communication circuitry 326) and the wireless 802.11 link with wireless access points 372. The wireless access points 372 are generally coupled to Ethernet switches 374 via 802.3 links. It is contemplated that the wireless communication modules 370 may communicate with the wireless access points 372 via any of the wireless protocols disclosed herein. Additionally or alternatively, the Ethernet switches 374 may generally communicate with Ethernet 358 via 802.3 link. Ethernet 358 is also in communication with the local server 352, allowing information and data to be communicated between the remote user device 350 and the support apparatus 14.

Referring again to FIG. 20, the support apparatus 14 is in communication with the remote server 354 and the local server 352 to obtain information about the patient for controlling the heat exchange system 10 as described further herein. Electronic medical records 380 are generally stored within the remote server 354 and may be accessed via the communication network 356.

The local server 352 may include an application or software allowing for information and data to the communicated between the various devices and systems of the medical facility, as well as between caregivers. The local server 352 includes a control unit 390 having a processor 392, a memory 394, and other control circuitry. Instructions or routines 396 are stored within the memory 394 executable by the processor 392. The control circuitry generally includes communication circuitry 398 allowing for bidirectional communication via the communication network 356. The medical facility may also include facility devices 400, such as computers at a nurse call station, to communicate with the local server 352 via Ethernet 358.

Figure 23:
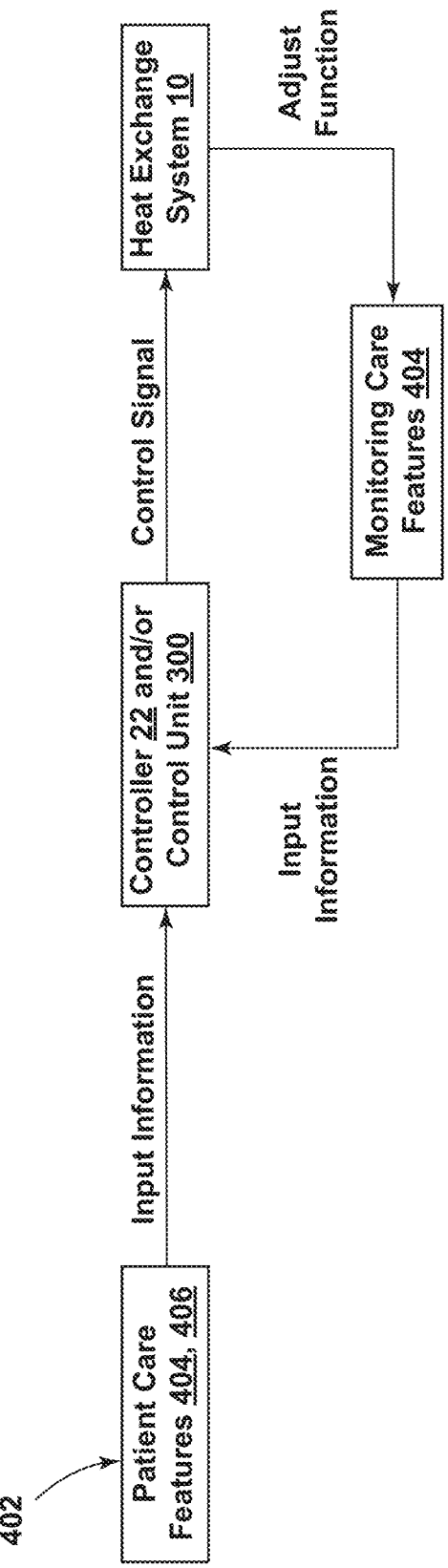
FIG. 23 is a block diagram of a closed loop system for controlling a heat exchange system, according to the present disclosure.

Referring still to FIG. 20, as well as FIG. 23, the various systems and devices may be in communication to create a closed-loop system for dynamically adjusting and controlling the heat exchange system 10. In such examples, all or part of the heat exchange system 10 may be activated, deactivated, or adjusted in response to a variety of information for regulating different zones for therapy and/or comfort.

Any configuration of the heat exchange system 10 can be dynamically adjusted. The more heating and cooling locations 16, 18 included in or affected by the heat exchange system 10, the more adaptive and reactive the heat exchange system 10 can be. For example, each configuration of the temperature regulating device 68 may be selectively activated, deactivated, and/or adjusted to maximize the comfort and therapeutic benefit to the patient.

At least one, but often multiple, patient care features 402 may provide an input to the controller 22 of the support apparatus 14 and/or the control unit 300 of the heat exchange system 10. The patient care features 402 may include monitoring features 404, which actively monitor information. In comparison, additional care features 406 do not actively monitor information and include information, such as, inputs by the caregiver, care protocols, and other information related to caring for the patient. The input from the patient care feature 402 is generally communicated between the controller 22 and the control unit 300 for adjusting the heat exchange system 10 in response to the input. The patient care features 402 may have a variety of configurations to provide information about the support apparatus 14, the patient, the patient room 182 or surgical suite 40, or any factor that can affect the care and comfort of the patient.

In various examples, the monitoring feature 404 may include the support apparatus 14 and the input includes information sensed by the support apparatus 14. The support apparatus 14 may include bed sensors, configured to sense the position of the support apparatus 14. The position of the support apparatus 14 affects the position of the patient and, consequently, pressure applied to various areas on the patient. For example, elevating the head of the patient can cause increased pressure on the sacral region, which is a high risk location for developing pressure injuries.

The support apparatus 14 also includes pressure sensors, which may be the position sensors 328 or additional pressure sensors. The pressure sensors may be configured as discrete sensors arranged across the support surface assembly 60, load cells, strain gauges, a pressure sensing mat, pressure-sensitive foam, etc. The pressure sensors may be embedded or integrated into the support surface assembly 60 in a manner that balances accurate pressure sensing data with reducing interface pressure between the pressure sensors and the patient.

The pressure sensors sense and provide pressure information (e.g., the input) to the controller 22 of the support apparatus 14. The pressure information may map the high pressure and low pressure areas between the patient and the support surface assembly 60. The high pressure areas may generally correlate to areas that are at higher risk for developing pressure injuries.

Further, the controller 22 may utilize the pressure information to determine the location of bony prominences and other high-risk locations for developing pressure injuries. These locations may be considered peak pressure locations or areas that are more susceptible to developing pressure injuries. This determination may be based on more generalized or standardized anthropometry and/or known locations of bony prominences.

Additionally or alternatively, this determination may be more customized to the patient based on information from the electronic medical record 380. For example, the height, weight, stature, etc. of the patient stored in the electronic medical record 380 may be factored into the determination of the controller 22. Moreover, the location of bony prominences may be inferred from sensed pressure information, which provides more personalization for the high-risk locations for the patient.

Determining and/or sensing these peak pressure locations may be advantageous for determining when an object is placed on the support apparatus 14, which can be sensed by the pressure sensors. For example, if a food tray is positioned on the support surface assembly 60, the controller 22 can compare the sensed pressure from the food tray to known or sensed locations of bony prominences. Based on this comparison, the controller 22 is configured to determine that, based on the position of the patient and peak pressure locations, the food tray is not part of the patient to be monitored. Accordingly, this additional object can be disregarded by the controller 22 when controlling the heat exchange system 10.

Referring still to FIGS. 20 and 23, the pressure information may determine a posture or orientation of the patient on the support surface assembly 60, which can also be used to determine the high risk areas and bony prominences relative the support surface assembly 60. For example, the controller 22 is configured to determine that the patient is in the supine position, on his or her side, sitting, etc. based on the pressure information. The posture or orientation of the patient alters the pressure distribution to various areas and can affect which bony prominences are at higher risk of developing a pressure injury (e.g., the sacral region when supine, a hip when on his or her side, etc.).

The support apparatus 14 may have a scale function to sense a weight of the patient. The weight of the patient may affect the interface pressure felt by the patient. Moreover, weight may be correlated with difficulty or efficiency of heating and cooling the patient.

Additionally or alternatively, the patient care feature 402 may include the MCM topper, which may provide moisture and temperature information. For example, the MCM system may have outlet sensors proximate to an outlet of the coverlet. The outlet sensors may be configured to sense moisture levels or temperature of the air. Higher moisture and temperature may be indicative of an increased risk of pressure injury development.

The patient care feature 402 may also include an imager within the patient room 182, which is configured to capture image data of the patient. The image data may be any still or video data. The imager may capture the image data, which can be processed and analyzed to determine a variety of patient information. The image data may be processed for posture recognition to determine the position of the patient (e.g., supine, sitting, etc.) on the support apparatus 14. The image data may also be utilized to determine the location of the patient on the support apparatus 14, such as closer to the head end, closer to the foot end, etc.

The imager may compare image data, such as multiple image frames, to determine movement of the patient. The imager may be configured to detect an object using edge detection and utilize image-based object recognition on the detected object. The movement of the patient may be determined and tracked by the change in shape or orientation of the patient between image frames. The imager may use any practicable image recognition and/or pose estimate techniques.

Moreover, the imager may include thermal imaging capabilities used for determining vital signs information or physiological parameters of the patient. The thermal imaging capabilities may be utilized to determine vital signs information, such as, but not limited to, core temperature, skin temperature, heart rate, and respiration rate.

Referring still to FIGS. 20 and 23, the patient care features 402 may be configured to directly interact with or contact the patient to determine vital signs information or other information about the patient. For example, the patient care features 402 may be configured to sense heart rate, respiration rate, skin temperature, core temperature, blood pressure, pulse oximetry, fetal information, etc. Accordingly, the patient care features 402 may be configured as heart rate monitors, ventilators, temperature sensors, blood pressure cuffs, finger clamps, fetal monitors, etc. The patient care feature 402 may be positioned on the patient, such as the finger clamp or blood pressure cuff. The patient care feature 402 may also be disposed on the support surface assembly 60, such as the temperature sensor printed on the outer ticking 72, or below the support surface assembly 60, such as contactless heart rate monitors between the support surface assembly 60 and the upper frame 186.

Further, the patient care feature 402 may be configured to determine information about the environment surrounding the patient. For example, the patient care feature 402 may include a room thermostat for the patient room 182 or surgical suite 40 to monitor the room temperature and any changes to the room temperature. The patient care feature 402 may also include humidity sensors for the patient room 182 or surgical suite 40. Further, the patient care feature 402 may also be a sunlight sensor disposed proximate to the patient. The amount of direct sunlight felt by the patient may affect the overall temperature and/or comfort of the patient. Information about the surrounding environment of the patient may affect the comfort of the patient, as well as efficacy of therapeutic treatments.

Further, the patient care feature 402 may include an accessory coupled to the support apparatus 14 or indicated in the electronic medical record 380. For example, the patient may utilize a warming blanket, which operates to warm the patient separate from the heat exchange system 10. The warming blanket may be similar to the blanket 110 or separate from the heat exchange system 10.

Moreover, the patient care feature 402 may not directly monitor information about the patient (e.g., the additional care features 406). A non-limiting example of this may include the electronic medical record 380. The electronic medical record 380 provides a variety of patient information, such as, but not limited to, anthropometry, caregiver notes and observations, treatment orders, conditions, medications, and other information about the patient to the controller 22. The electronic medical record 380 may also include specific pressure injury information, such as scores related to the likelihood of developing a pressure injury, in what area or areas pressure injuries are more likely to develop, and procedures or devices that may affect the likelihood of developing a pressure injury. The additional care features 406 that do not directly monitor information but affect the care of the patient also include, but are not limited to, treatment protocols, facility protocols, building architecture (e.g., outside window location, cardinal direction of windows for sun, etc.), etc.

A variety of factors affect the patient and can be directly monitored and/or input by the caregiver and communicated to the controller 22 to be factored into the control of the heat exchange system 10. In addition to the patient care devices 402 disclosed herein, the patient care features 402 that may provide input information (directly or via caregiver input) to adjust the heat exchange system 10 may also include, but are not limited to heart rate monitors, patient temperature devices, ventilators, blood pressure devices, pulse oximetry devices, vital sign monitors, fetal monitors, esophageal probes (e.g., to monitor core temperature), ventilators, catheter monitor Foley probes (e.g., to monitor core temperature), arctic sun coolers, electrocardiography (ECG) devices, hospital room thermostat, temperature sensors in mattress overlays, temperature sensors integrated into a mattress or support surface assembly 60, thermal cameras or imagers, Forward Looking InfraRed Infrared (FLIR) monitoring of the patient, heat lamps or war mining lights in hospital rooms such as surgical suites, bispectral index (BIS) monitors for monitoring depth of anesthesia/sedation when using paralytics and which could affect core or skin temperature, extracorporeal membrane oxygenation (ECMO) devices, sequential compression devices, mass blood transfusers, intravenous (IV) pumps, dialysis machines, intracranial pressure monitors, televisions, computers, computer monitors, and any other equipment in the room. The patient care devices 402 may affect temperature of the patient or the area surrounding the patient and/or monitor the temperature of the patient or the surrounding areas, which can each affect the function of the heat exchange system 10.

Referring still to FIGS. 20 and 23, the patient care features 402 provide information to the controller 22 and/or the control unit 300. The input information may be provided directly by the patient care features 402 or retrieved by the controller 22 and/or control unit 300. At least one of the controller 22 and the control unit 300 is configured to compile and analyze the inputs from the patient care feature.

In at least one example, the controller 22 includes an algorithm (i.e., routines 324) that processes the inputs from the various patient care features 402. The controller 22 is configured to determine whether all or a portion of the heat exchange system 10 is to be adjusted based on the various inputs. For example, the patient may slide toward the foot end of the support apparatus 14, and the areas being cooled may be adjusted to better align with the new position of the higher risk areas. In another example, the room temperature may increase with the afternoon sun, so the heat exchange system 10 may reduce or deactivate any heating function, while continuing to cool high-risk areas. In an additional non-limiting example, when the patient is using the warming blanket, the heat exchange system 10 may not operate to warm the patient. These examples are merely exemplary and are not limiting.

At least one of the control unit 300 and the controller 22 is configured to determine how to adjust the heat exchange system 10. Based on the control signal from the controller 22 or the control unit 300, the heat exchange system 10 is configured to adapt or react to the input information. The adjustment to the heat exchange system 10 may result from the temperature provided by the thermoelectric device 12, the compressor 160 with the heating and cooling loops 162, 164, and/or the thermoelectric modules 202 being increased or decreased based on the current or power provided to the temperature regulating devices 68. Moreover, the temperature regulating devices 68 may be activated or deactivated. The temperature effect felt by the patient may additionally or alternatively be adjusted through airflow. For example, the fan 20 and/or the temperature control fan 176 may draw air away from the patient, through the airflow channels 216 in the support structure 204, and/or through the MCM topper at a higher rate to create a greater cooling effect on the patient.

After the adjustment of the heat exchange system 10 in response to the inputs, the patient continues to be monitored by the caregiver and monitoring features 404. The monitoring features 404 that actively and/or more directly monitor the patient are configured to continue to sense information about the patient and communicate the information to the controller 22 and/or the control unit 300 as subsequent inputs, providing a feedback loop that controls the operation of the heat exchange system 10. The controller 22 may also be configured to continually retrieve updated information input by the caregiver. The information that may be monitored by the patient care features 402 may include, but are not limited to, patient position (e.g., supine, sitting, etc.), patient location on the support apparatus 14, location of bony prominences, skin temperature, core temperature, pressure levels (e.g., high, low, changing, etc.), etc.

Moreover, the heating and cooling functions may operate to maintain a predefined core temperature of the patient and predefined skin temperatures at the high-risk locations. The patient care features 402 may be configured to sense the core temperature and the skin temperature. The controller 22 is configured to adjust the function of the heat exchange system 10 to maintain the core temperature and skin temperature at the high-risk locations.

The heat exchange system 10 is configured to be continually and dynamically adjusted in response to the patient. This configuration optimizes comfort and therapeutic care provided to the patient. The cooling and heating functions of the heat exchange system 10 may be customized to the patient, as well as reactive to changes to the patient and/or the surrounding environment.

Referring to FIGS. 20 and 23, the heat exchange system 10 may be reactive in different ways based on different modes of operations. For example, the heat exchange system 10 may be operated in a normothermia mode. In the normothermia mode, the heat exchange system 10 may operate to cool the high-risk areas, as well as warm the patient to maintain normothermia. In a skin-based mode, the heat exchange system 10 may operate to cool the high-risk areas, without operating to warm the patient. The skin-based mode may be advantageous for when the controller 22 determines that the patient is sufficiently warm based on the various inputs, such as, for example, room temperature, core temperature, warming blanket, etc. The controller 22 and/or the control unit 300 may be configured to automatically adjust between different modes of operations based on the inputs received from the patient care features 402. Additionally or alternatively, the caregiver may assign the mode of operation.

Figure 25:
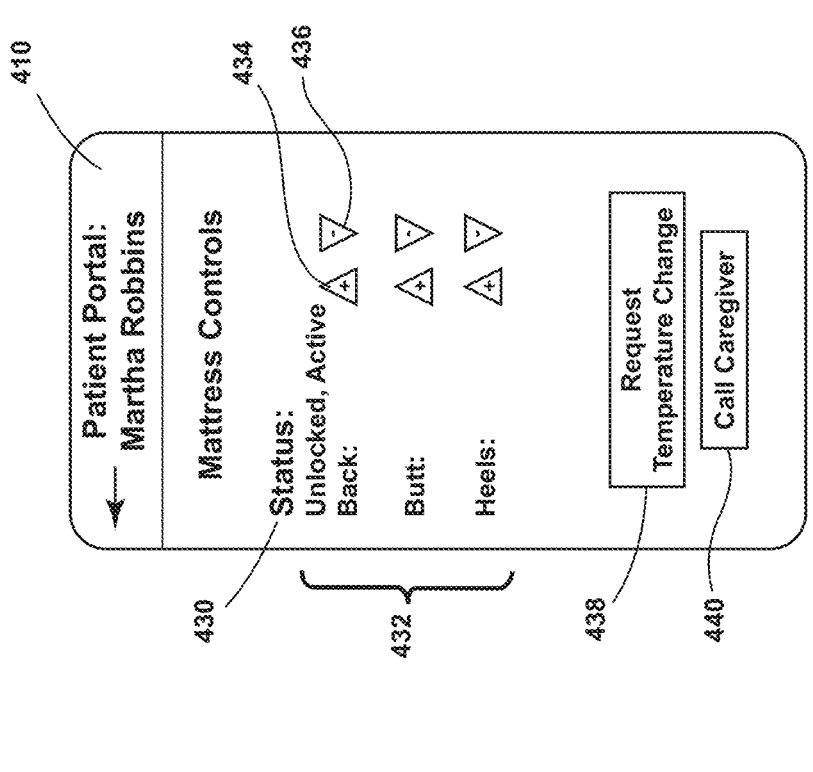
FIG. 25 is illustrative of an application interface for a patient displaying information about a heat exchange system, according to the present disclosure.
Figure 24:
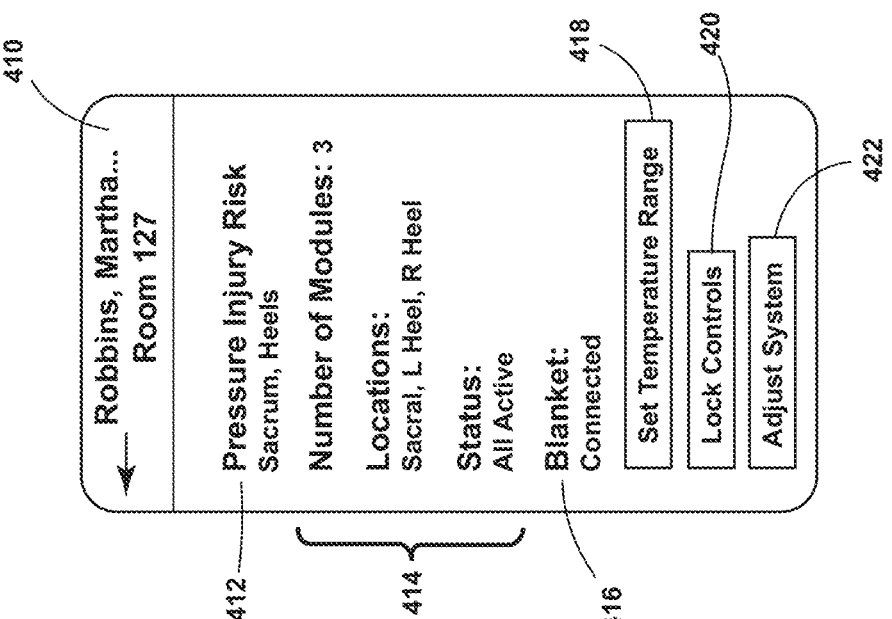
FIG. 24 is illustrative of an application interface for a caregiver displaying information about a heat exchange system, according to the present disclosure.

Referring again to FIG. 20, as well as FIGS. 24 and 25, the caregiver and the patient may control the heat exchange system 10 through various devices separate from the support apparatus 14, such as the facility devices 400 and the remote user device 350. The remote user device 350 may be a phone, tablet, wearable device, laptop, computer, or other devices that may belong to the medical facility, the caregiver, or the patient.

Each of the devices for controlling the heat exchange system 10 may include an application or software utilized for displaying an application interface 410. The application interface 410 may be used to communicate information and make adjustments to the heat exchange system 10. Additionally or alternatively, the application interface 410 may be configured to receive inputs related to the heat exchange system 10.

As illustrated in FIG. 24, the application interface 410 may be specific for the caregiver where the caregiver may view or control various aspects of the heat exchange system 10. The application interface 410 displays a variety of information relating to the heat exchange system 10. For example, the application interface 410 may display risk information 412, which may show areas of the patient that are at an increased chance of developing the pressure injury. The caregiver may input this information and/or the information may be automatically populated from the electronic medical record 380.

The application interface 410 may also include system details 414. In the illustrated example, the system details 414 may include the number of thermoelectric devices 12 or thermoelectric modules 202 within the support apparatus 14. In examples using other configurations of the heat exchange system 10, the system details 414 may include the type of heat exchange system 10, the position of the various cooling locations or heating locations on the patient, etc.

In the illustrated example, the thermoelectric modules 202 are located in the sacral region 234 and the lower extremity regions 240, 242 of the patient and all the thermoelectric modules 202 are active. The caregiver may utilize the application interface 410 to determine where the patient is receiving treatment from the heat exchange system 10, and whether the heat exchange system 10 is activated. The application interface 410 may also include accessory information 416. The accessory information 416 may include details about the accessories, associated heat exchange system 10, the type of accessories, length of time of use of the accessories etc. In the illustrated example, the accessory information 416 includes that the blanket 110 is being utilized with the heat exchange system 10.

The application interface 410 may also have a variety of selectable features that the caregiver may utilize for controlling the heat exchange system 10. For example, the application interface 410 includes a temperature setting feature 418. The caregiver may set upper and lower temperature boundaries for specific areas on the patient through the temperature setting feature 418. For example, areas that are at higher risk for developing pressure injury may have a predefined temperature range that is a lower temperature range than other areas. Additionally, the heated regions may have predefined temperature ranges that are set by the caregiver. The predefined temperature ranges may be defined based on therapeutic limits based on the treatment for the patient.

The application interface 410 may also include a lock feature 420. When the caregiver selects the lock feature 420, thereby inputting a lock command, the heat exchange system 10 may be locked to the patient, such that the patient may not adjust select aspects or any aspect of the heat exchange system 10. Additionally, the application interface 410 includes an adjustment feature 422. The adjustment feature 422 allows the caregiver to adjust other aspects of the heat exchange system 10, such as, for example, the location of the temperature regulating device 68, an addition or removal of an accessory, etc. The information and features on the application interface 410 in FIG. 23 are merely exemplary and may include any practicable information for the caregiver.

Figure 26:
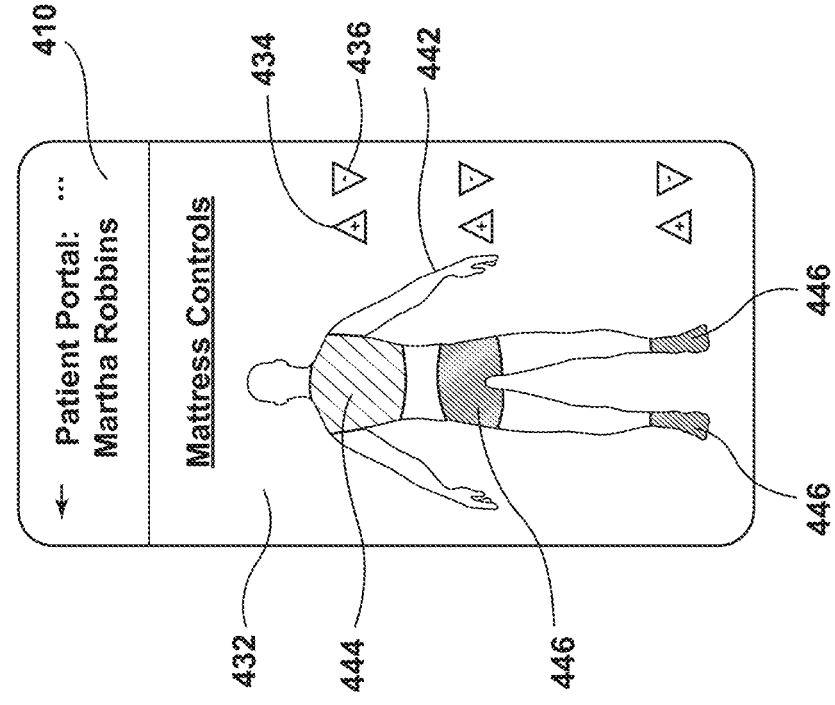
FIG. 26 is illustrative of an application interface for a patient providing a graphical illustration of temperature effects, according to the present disclosure.

Referring to FIGS. 25 and 26, the application interface 410 may be specific for the patient where the patient may view or control various aspects of the heat exchange system 10. The application interface 410 may include status information 430 of the heat exchange system 10. The illustrated example, the status information 430 indicates that the heat exchange system 10 is unlocked so that the patient may adjust aspects of the heat exchange system 10, and that the heat exchange system 10 is currently active (e.g., warming and/or cooling).

The application interface 410 may also include adjustment features 432 for adjusting the various temperature regulating devices 68 incorporated into the heat exchange system 10. For example, the three locations of the temperature regulating devices 68 are presented to the patient along with an increase feature 434 and a decrease feature 436. The three areas presented to the patient in the example illustrated in FIG. 25 include the back, butt, and heels. The patient may increase the temperature of a specific area using the increase feature 436 and decrease the temperature of an area using the decrease feature 436. For example, the application interface 410 may receive a first input from the patient relating to one of the thermoelectric modules 202 (e.g., positioned at the back of the patient) and a second input relating to another thermoelectric modules 202 (e.g., positioned at the heels of the patient). The increasing and decreasing may be controlled by the user within the limits set by the caregiver. The limits are generally designed for therapeutic treatment purposes and therefore may not be adjusted outside of the limit by the patient.

Further, adjustment of the heat exchange system 10 may be locked by the caregiver, thereby locking patient control of the temperature effects generated by the heat exchange system 10. Locking the patient controls may be advantageous for providing the selected therapy or treatment to the patient without the patient affecting the outcome by adjusting the temperature effect. Further, certain aspects of the heat exchange system 10 may be locked, while other aspects are unlocked. In such examples, the locked aspects may relate to high-risk areas receiving therapy by cooling the area, while the unlocked aspects may relate to areas being warmed by the heat exchange system 10.

In various aspects, the patient control may be automatically unlocked under certain circumstances. For example, when the controller 22 determines that the movement of the patient exceeds the predefined threshold, as sensed by the position sensors 328, the controller 22 may automatically unlock the patient controls. The patient may again control the temperature of the heat exchange system 10 within the therapeutic limits. This may be advantageous as movement of the patient reduces the risk of pressure injury development and, therefore, the activated treatment may be paused or ceased automatically. If the movement falls below the predefined threshold, the heat exchange system 10 may automatically be locked to reactivate the treatment provided by the heat exchange system 10.

The application interface 410 may also include selectable features for the patient. The application interface 410 may include a request feature 438 that allows the patient to request a change in the temperature range of the heat exchange system 10. The temperature change may also be utilized for requesting a deactivation or a change in location of the temperature regulating devices 68. Additionally, the application interface 410 may include a call feature 440 allowing the patient to call the caregiver.

In the example illustrated in FIG. 26, the application interface 410 may provide an avatar or a graphical representation 442 of the patient. The graphical representation 442 may highlight or illustrate heating zones 444 and cooling zones 446. The heating zones 444 indicate the areas currently being heated by the heat exchange system 10, the cooling zones 446 indicate areas currently being cooled by the heat exchange system 10, and other areas of the graphical representation 442 may not be directly affected by the heat exchange system 10. The indication of the heating and cooling zones 444, 446 may be through different colors, shading, imaging, patterns, indicators, etc. Further, the graphical representation 442 may also illustrate where various deactivated components, such as deactivated thermoelectric modules 202, are positioned.

The patient may control the heat exchange system 10 through the application interface 410 having the graphical representation 442. In the illustrated example, each of the heating zones 444 and the cooling zones 446 are associated with the increase feature 434 and the decrease feature 436, respectively. The patient may also activate or deactivate zones 444, 446 by pressing or touching an area of the graphical representation 442. Further, the application interface 410 may include temperature information for each of the heating zones 444 and the cooling zones 446 as sensed by the temperature sensors 174, as well as other sensed information utilized to control and adjust the heat exchange system 10 as described herein. Other methods of controlling the heat exchange system 10 may be utilized without departing from the teachings herein. The information and features on the application interface 410 in FIGS. 25 and 26 are merely exemplary and may include any practicable information for the caregiver.

Referring to FIGS. 1-26, the heat exchange system 10 may provide a multi-zone thermal regulation system for the patient. The heat exchange system 10 may be utilized for increasing the comfort of the patient while providing treatment or therapy to the patient. Oftentimes, select areas 24 on the patient may be maintained at a lower temperature to prevent pressure injuries while other areas 26 of the patient may be warmed to maintain normothermia or comfort for the patient. The warmed areas 26 are areas that are not at risk or less at risk of developing pressure injuries and do not interfere with other treatment to the patient or the surgical site. The heat exchange system 10 may also cool higher risk areas without warming the patient.

Additionally, the heat exchange system 10 may be used to increase the comfort of the patient while providing therapeutic benefits related to pressure injury development. For example, due to the neuropathy or physiology of certain patients, certain portions of the body may experience different temperatures. In certain aspects, extremities may feel cold while the body core feels warm. In additional aspects, the use of an intravenous (IV) therapies may contribute to a cooling sensation. The heat exchange system 10 may provide balance for the thermal regulation of the patient and prevent overheating or sweat in areas that can lead to pressure injuries. The heat exchange system 10 disclosed herein may assist in thermal regulation that affects the comfort of the patient and which may lead to therapeutic concerns.

The heat exchange system 10 may be utilized to simultaneously cool select areas 24 while warming other areas 26 on the patient to provide both comfort and therapy for the patient. The temperature regulating device 68 generally generates heat when producing the cooling temperature effect, and the heat exchange system 10 may reclaim the generated heat to warm the patient. Further, the heat exchange system 10 may include various components that may be single use or single patient use, such as the skin dressing 142, the tubing 100, etc.

Additionally or alternatively, an x-ray sleeve 450 (see FIG. 14) may be utilized with the heat exchange system 10. The x-ray sleeve 450 may be placed above the temperature regulating devices 68 to prevent interference with x-ray equipment. For example, in examples with the thermoelectric modules 202, the one or more x-ray sleeves 450 may be positioned over each thermoelectric module 202 or alternatively may extend across the core 70 and the thermoelectric modules 202 within the outer ticking 72.

Use of the present system and devices will provide for a variety of advantages. For example, the heat exchange system 10 may be integrated into the support apparatus 14 or may be a separate assembly that may be used in conjunction with the support apparatus 14. Further, the heat exchange system 10 may be utilized with various configurations of support apparatus 14. Additionally, the heat exchange system 10 may be interchangeable and adjustable with other aspects of the support apparatus 14 to provide different or customizable treatment for the patient. Additionally, the patient may control the heat exchange system 10 within therapeutic limits set by the caregiver to increase the comfort and overall care of the patient. Further, the heat generated by the temperature regulating device 68 may be utilized in the heat exchange system 10 to form a closed system.

Moreover, the heat exchange system 10 may provide multi-zone treatment having different temperature effects across the multiple zones. Also, the heat exchange system 10 may simultaneously or concurrently cool select areas 24 on the patient and heat other areas 26. Further, the heat exchange system 10 may be a separate assembly or may be integrated into the support apparatus 14. Additionally, the heat exchange system 10 may be utilized with additional accessories that may provide heating or cooling temperature effects to the support apparatus 14, the patient, and/or the caregiver. Also, an integrated heat exchange system 10 may assist with the management of lines and equipment. Additional benefits or advantages may be realized and/or achieved.

Each of the controller 22 and the control units 300, 390 disclosed herein may include various types of control circuitry, digital or analog, and may each include a processor, a microcontroller, an application specific integrated circuit (ASIC), or other circuitry configured to perform the various inputs or outputs, control, analysis, or other functions described herein. The memories 304, 322, 394 described herein may be implemented in a variety of volatile and nonvolatile memory formats. Routines 306, 324, 396 may include operating instructions to enable the various methods described herein.

The device disclosed herein is further summarized in the following paragraphs and is further characterized by combinations of any and all of the various aspects described therein.

According to another aspect of the present disclosure, a heat exchange system includes at least one thermoelectric device operably coupled with a support apparatus. The at least one thermoelectric device is configured to reduce a temperature at a first location and increase a temperature at a second location different than the first location. A heat directing feature is disposed proximate to the at least one thermoelectric device. The heat directing feature is configured to direct heat generated by the at least one thermoelectric device toward the second location. A controller is communicatively coupled with the at least one thermoelectric device. The controller is configured to activate the at least one thermoelectric device to reduce the temperature at the first location and concurrently increase the temperature at the second location. The first location is configured to align with a first area on a patient and the second location is configured to align with a second area on the patient.

According to another aspect, a patch is configured to be coupled to a first area of the patient and a thermally conductive connector extends between the patch and at least one thermoelectric device to reduce the temperature at the first area.

According to another aspect, a thermally conductive spacer is configured to be disposed in a cavity of a support surface assembly on a support apparatus. The thermally conductive spacer is positioned at a first location and in thermal communication with at least one thermoelectric device.

According to another aspect, a patient care feature is communicatively coupled to a controller. The patient care feature is configured to communicate information relating to at least one of a patient, a surrounding environment, and a monitoring device. The controller is configured to adjust at least one of a heating function and a cooling function of a thermoelectric device based on the information from the patient care feature.

According to another aspect, a tubing extends between a heat directing feature and a second location. The heat directing feature is a fan. The fan directs air through the tubing to a second location.

According to another aspect, a blanket has an internal cavity. Air is directed through a tubing and into the blanket. A second location is an area in contact with the blanket.

According to another aspect, a resistive element is disposed within a tubing to increase an air temperature of air traveling through the tubing.

According to another aspect, a heat directing feature is a fan. The fan is configured to direct heat generated by at least one thermoelectric device to increase a temperature at the second location.

According to another aspect, a thermally conductive connector extends through a support surface assembly between a heat directing feature and a second location. The thermally conductive connector is configured to transfer heat generated by at least one thermoelectric device to a second location.

According to another aspect, a first support structure is disposed at a first location. A second support structure is disposed at a second location. Each of the first support structure and the second support structure defines an airflow channel. At least one thermoelectric device includes a first thermoelectric device coupled to the first support structure and a second thermoelectric device coupled to the second support structure.

According to another aspect, a controller is configured to direct a current in a first direction through a first thermoelectric device to reduce a temperature at a first location and a current through a second thermoelectric device in a second direction to increase a temperature at a second location.

According to another aspect, a support surface assembly includes an outer ticking. A core is disposed within the outer ticking, and the core defines an insertion cavity. A heat exchange system is coupled to the core. The heat exchange system includes a thermally conductive spacer selectively insertable in the insertion cavity. A thermoelectric device is disposed adjacent to the thermally conductive spacer. The thermoelectric device reduces a temperature at a first location via the thermally conductive spacer. A fan is configured to direct heat generated by the thermoelectric device away from the thermoelectric device. A connector extends from the fan to a second location. The connector is thermally conductive and configured to transfer the heat to the second location and, consequently, increase a temperature at the second location.

According to another aspect, a connector extends through a core.

According to another aspect, a heat exchange system includes cooling fins coupled to a thermoelectric device and positioned between the thermoelectric device and a fan.

According to another aspect, a support apparatus includes a frame. A support surface assembly is disposed on the frame and configured to support a patient. A rail is coupled to the frame. A heat exchange system is selectively coupled to the rail. The heat exchange system includes a skin dressing configured to be coupled to the patient. A thermally conductive connector is coupled to the skin dressing. A thermoelectric device is coupled to the thermally conductive connector and configured to reduce a temperature of the skin dressing. The thermoelectric device generates heat. A tubing is coupled to the thermoelectric device and configured to guide heated air warmed by the heat generated by the thermoelectric device to a second location.

According to another aspect, a tubing is configured to couple to an inlet port of a forced-air blanket.

According to another aspect, a heat exchange system includes a fan coupled to a thermoelectric device to direct air through a tubing.

According to another aspect, a heat exchange system includes a resistive element coupled to a tubing to generate additional heat.

According to another aspect, a support apparatus includes a frame having a deck for supporting a patient thereon. A heat exchange system is coupled to the frame. The heat exchange system includes a compressor. Heating loops are coupled to the compressor, where the heating loops extend along a first location on the deck. Cooling loops are coupled to the compressor where the cooling loops extend along a second location on the deck. The compressor drives a fluid through the heating loops and the cooling loops.

According to another aspect, heating loops and cooling loops are disposed in a topper.

According to another aspect, a heat exchange system includes a tubing extending between a compressor and an accessory to direct heated air to the accessory.

According to another aspect, a heat exchange system includes a heater element operably coupled to at least one of the compressor and the accessory.

According to another aspect, a heat exchange system includes a hose extending between a compressor and an accessory to direct cooled air to the accessory.

According to another aspect, a support surface assembly includes a core defining a first insertion cavity and a second insertion cavity. An outer ticking extends over the core. A first thermoelectric module is selectively disposed within the first insertion cavity. A second thermoelectric module is selectively disposed within the second insertion cavity. Each of the first thermoelectric module and the second thermoelectric module include a support structure defining an airflow channel. A thermoelectric device is coupled with the support structure. A fan is coupled to the support structure and configured to direct air through the airflow channel. A controller is in communication with the first thermoelectric module and the second thermoelectric module. The controller is configured to selectively and independently direct a current through the first thermoelectric module and the second thermoelectric module to adjust a temperature of a corresponding area of the outer ticking.

According to another aspect, a thermoelectric device of a first thermoelectric module is configured to cool a first location of an outer ticking. A thermoelectric device of a second thermoelectric module is configured to heat a second location of the outer ticking.

According to another aspect, thermoelectric devices are elongated features extending through support structures, respectively.

According to another aspect, a topper is disposed over a core, a first thermoelectric module, and a second thermoelectric module.

According to another aspect, an outer ticking defines vents in fluid communication with a first thermoelectric module and a second thermoelectric module.

According to another aspect, a core includes a first layer and a second layer separated by a spacer.

According to another aspect, a spacer is air permeable. Air directed by the fan is moved through the spacer.

According to another aspect, a patient temperature regulating system includes a first thermoelectric module having a first thermoelectric device. A second thermoelectric module has a second thermoelectric device. At least one user device is configured to receive an input. A controller is in communication with each of the first thermoelectric module, the second thermoelectric module, and the at least one user device. The controller is configured to receive a first input relating to the first thermoelectric module from the at least one user device, direct a current in a first direction through the first thermoelectric device to produce a first temperature effect, receive a second input relating to the second thermoelectric module from the at least one user device, and direct a current in a second direction through the second thermoelectric device to produce a second temperature effect.

According to another aspect of the present disclosure, at least one of a first input and a second input is a lock command configured to prevent adjustment of a first thermoelectric module and a second thermoelectric module.

According to another aspect of the present disclosure, a controller is configured to produce a first temperature effect and a second temperature effect simultaneously.

According to another aspect of the present disclosure, a first temperature effect is a cooling effect and a second temperature effect is a warming effect.

According to another aspect of the present disclosure, at least one user device includes a connected device and a pendant device coupled to a support apparatus.

According to another aspect of the present disclosure, at least one user device includes a connected device coupled to a support apparatus and a remote user device.

A means for exchanging heat includes at least one thermoelectric means coupled with a support means. The thermoelectric means is configured to reduce a temperature at a first location and increase a temperature at a second location different than the first location. A means for blowing is disposed adjacent to the thermoelectric means. The means for blowing is configured to direct heat generated by the thermoelectric means away from the thermoelectric means. A control means is communicatively coupled to the thermoelectric means and the means for blowing. The control means is configured to activate at least one of the thermoelectric means and the means for blowing to reduce the temperature at the first location and concurrently increase the temperature at the second location. The first location is configured to align with a first area on a patient and the second location is configured to align with a second area on the patient.

It will be understood by one having ordinary skill in the art that construction of the described disclosure and other components is not limited to any specific material. Other exemplary embodiments of the disclosure disclosed herein may be formed from a wide variety of materials, unless described otherwise herein.

For purposes of this disclosure, the term "coupled" (in all of its forms, couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such joining may be permanent in nature or may be removable or releasable in nature unless otherwise stated.

It is also important to note that the construction and arrangement of the elements of the disclosure, as shown in the exemplary embodiments, is illustrative only. Although only a few embodiments of the present innovations have been described in detail in this disclosure, those skilled in the art who review this disclosure will readily appreciate that many modifications are possible (e.g., variations in sizes, dimensions, structures, shapes, and proportions of the various elements, values of parameters, mounting arrangements, use of materials, colors, orientations, etc.) without materially departing from the novel teachings and advantages of the subject matter recited. For example, elements shown as integrally formed may be constructed of multiple parts, or elements shown as multiple parts may be integrally formed, the operation of the interfaces may be reversed or otherwise varied, the length or width of the structures and/or members or connector or other elements of the system may be varied, the nature or number of adjustment positions provided between the elements may be varied. It should be noted that the elements and/or assemblies of the system may be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary embodiments without departing from the spirit of the present innovations.

It will be understood that any described processes or steps within described processes may be combined with other disclosed processes or steps to form structures within the scope of the present disclosure. The exemplary structures and processes disclosed herein are for illustrative purposes and are not to be construed as limiting.

What is claimed is:

1. A support surface assembly, comprising:
an outer ticking;
a core disposed within the outer ticking, wherein the core defines an insertion cavity; and
a heat exchange system coupled to the core, wherein the heat exchange system includes:
a thermally conductive spacer selectively insertable in the insertion cavity;
a thermoelectric device disposed adjacent to the thermally conductive spacer, wherein the thermoelectric device reduces a temperature at a first location of said support surface assembly via the thermally conductive spacer for cooling a first area of a person supported on said support surface assembly;
a fan configured to direct heat generated by the thermoelectric device away from the thermoelectric device; and
a connector extending from the fan to a second location of said support surface assembly, wherein the connector is thermally conductive to form a thermal path to transfer and redirect the heat generated by the thermoelectric device to the second location of said support surface assembly and, consequently, utilize the heat generated by the thermoelectric device to increase a temperature at the second location for heating a second area of the person.

2. The support surface assembly of claim 1, wherein the connector extends through the core.

3. The support surface assembly of claim 1, wherein the heat exchange system includes cooling fins coupled to the thermoelectric device and positioned between the thermoelectric device and the fan.

4. The support surface assembly of claim 1, wherein the connector extends through the core at the first location and through the core toward a support surface of the outer ticking at the second location.

5. The support surface assembly of claim 1, wherein the connector is coupled to the fan.

6. A support surface assembly, comprising:
an outer ticking defining an interior;
a core including core blocks arranged in the interior to form a first insertion cavity and a second insertion cavity, wherein the outer ticking extends over the core;
a first thermoelectric module selectively disposed within the first insertion cavity;
a second thermoelectric module selectively disposed within the second insertion cavity, wherein the core blocks are configured to be interchanged between different positions within the interior to change locations of the first and second insertion cavities to, consequently, change locations of the first and second thermoelectric modules, and wherein each of the first thermoelectric module and the second thermoelectric module is a self-contained and removable unit that includes:
a support structure defining an airflow channel;
a thermoelectric device coupled with the support structure; and
a fan coupled to the support structure and configured to direct air through the airflow channel; and a controller in communication with the first thermoelectric module and the second thermoelectric module, wherein the controller is configured to selectively and independently direct a current through the first thermoelectric module and the second thermoelectric module to adjust a temperature of a corresponding area of the outer ticking.

7. The support surface assembly of claim 6, wherein the thermoelectric device of the first thermoelectric module is configured to cool a first location of the outer ticking, and wherein the thermoelectric device of the second thermoelectric module is configured to heat a second location of the outer ticking.

8. The support surface assembly of claim 6, wherein the thermoelectric devices are elongated features extending through the support structures, respectively.

9. The support surface assembly of claim 6, further comprising:

a topper disposed over the core, the first thermoelectric module, and the second thermoelectric module, wherein the topper extends over the core, the first thermoelectric module, and the second thermoelectric module.

10. The support surface assembly of claim 6, wherein the outer ticking defines vents in fluid communication with the first thermoelectric module and the second thermoelectric module.

11. The support surface assembly of claim 6, wherein the core includes a first layer and a second layer separated by a spacer.

12. The support surface assembly of claim 11, wherein the spacer is air permeable, and wherein the air directed by the fan is moved through the spacer.

13. The support surface assembly of claim 6, wherein for each of the first thermoelectric module and the second thermoelectric module the thermoelectric device includes a first portion extending through the support structure and a second portion disposed in the airflow channel.

14. The support surface assembly of claim 6, wherein the controller is configured to concurrently direct a current in a first direction through the first thermoelectric module and direct a current in a second direction through the second thermoelectric module to concurrently heat a first location of said support surface assembly with the first thermoelectric module and cool a second location of said support surface assembly with the second thermoelectric module.

15. The support surface assembly of claim 6, wherein the outer ticking defines at least one air vent, and wherein the first and second thermoelectric modules are enclosed within the interior of the outer ticking and in fluid communication with the at least one air vent.

* * * * *